US009693953B2

(12) United States Patent
Chollet et al.

(10) Patent No.: US 9,693,953 B2
(45) Date of Patent: *Jul. 4, 2017

(54) METHOD OF TREATING ATROPHIC VAGINITIS

(76) Inventors: Janet A. Chollet, Newton Center, MA (US); Fred H. Mermelstein, West Newton, MA (US); Bernadette Klamerus, Carmichaels, PA (US)

( * ) Notice: Subject to any disclaimer, the term of this patent is extended or adjusted under 35 U.S.C. 154(b) by 372 days.

This patent is subject to a terminal disclaimer.

(21) Appl. No.: 11/757,787

(22) Filed: Jun. 4, 2007

(65) Prior Publication Data
US 2008/0026035 A1  Jan. 31, 2008

Related U.S. Application Data

(60) Provisional application No. 60/810,715, filed on Jun. 2, 2006, provisional application No. 60/917,800, filed on May 14, 2007.

(51) Int. Cl.
| A61K 9/02 | (2006.01) |
| A61K 31/215 | (2006.01) |
| A61P 15/02 | (2006.01) |
| A61K 31/56 | (2006.01) |
| A61K 9/00 | (2006.01) |
| A61K 47/02 | (2006.01) |
| A61K 47/14 | (2017.01) |
| A61K 47/22 | (2006.01) |
| A61K 31/57 | (2006.01) |

(52) U.S. Cl.
CPC ........... *A61K 9/0034* (2013.01); *A61K 9/02* (2013.01); *A61K 31/215* (2013.01); *A61K 31/56* (2013.01); *A61K 31/57* (2013.01); *A61K 47/02* (2013.01); *A61K 47/14* (2013.01); *A61K 47/22* (2013.01)

(58) Field of Classification Search
None
See application file for complete search history.

(56) References Cited

U.S. PATENT DOCUMENTS

| 4,894,373 A * | 1/1990 | Young .................. 514/239.2 |
| 5,189,212 A * | 2/1993 | Ruenitz .................. 562/468 |
| 5,543,150 A | 8/1996 | Bologna et al. |
| 5,558,877 A * | 9/1996 | Matlin et al. .................. 424/432 |
| 5,610,167 A | 3/1997 | Cullinan |
| 5,747,058 A | 5/1998 | Tipton et al. |
| 5,789,442 A | 8/1998 | Garfield et al. |
| 5,977,158 A | 11/1999 | Rasmussen |
| 6,107,331 A | 8/2000 | MacLean et al. |
| 6,165,491 A | 12/2000 | Grasset et al. |
| 6,306,914 B1 | 10/2001 | DeZiegler et al. |
| 6,355,670 B1 | 3/2002 | MacLean et al. |
| 6,469,016 B1 | 10/2002 | Place et al. |
| 6,482,448 B2 | 11/2002 | Tabor |
| 6,583,129 B1 | 6/2003 | Mazer et al. |
| 6,593,317 B1 | 7/2003 | DeZiegler et al. |
| 6,613,796 B2 | 9/2003 | MacLean et al. |
| 6,660,726 B2 | 12/2003 | Hill et al. |
| 6,708,822 B1 | 3/2004 | Muni |
| 6,747,018 B2 | 6/2004 | Tanabe et al. |
| 6,855,703 B1 | 2/2005 | Hill et al. |
| 6,911,438 B2 | 6/2005 | Wright |
| 7,018,992 B2 | 3/2006 | Koch et al. |
| 7,186,706 B2 | 3/2007 | Rosario-Jansen et al. |
| 7,405,303 B2 | 7/2008 | Hoekstra et al. |
| 7,414,043 B2 | 8/2008 | Kosemund et al. |
| 7,429,576 B2 | 9/2008 | Labrie |
| 7,442,833 B2 | 10/2008 | Eaddy, III et al. |
| 2001/0031747 A1 | 10/2001 | DeZiegler et al. |
| 2002/0012710 A1 | 1/2002 | Lansky |
| 2002/0013327 A1 | 1/2002 | Lee et al. |
| 2002/0103223 A1 | 8/2002 | Tabor |
| 2002/0128276 A1 | 9/2002 | Day et al. |
| 2002/0137749 A1 | 9/2002 | Levinson et al. |
| 2002/0169150 A1 | 11/2002 | Pickar |
| 2002/0173499 A1 | 11/2002 | Pickar |
| 2002/0173510 A1 | 11/2002 | Levinson et al. |
| 2002/0198179 A1 | 12/2002 | Labrie |
| 2003/0021859 A1 | 1/2003 | Tabor |
| 2003/0040510 A1 | 2/2003 | Labrie |
| 2003/0065008 A1 | 4/2003 | Labrie |
| 2003/0083228 A1 | 5/2003 | Carpino et al. |
| 2003/0125319 A1 | 7/2003 | Day et al. |
| 2004/0009994 A1 | 1/2004 | MacLean et al. |
| 2004/0044080 A1 * | 3/2004 | Place et al. .................. 514/573 |
| 2004/0092583 A1 | 5/2004 | Shanahan-Prendergast |
| 2004/0101557 A1 | 5/2004 | Gibson et al. |

(Continued)

FOREIGN PATENT DOCUMENTS

| CN | 1539410 | 10/2004 |
| CN | 1654037 A | 8/2005 |
| EP | 0792640 | 9/1997 |
| EP | 0 955 042 A1 | 11/1999 |
| EP | 1 652 535 A1 | 5/2006 |
| EP | 1199069 | 10/2006 |
| WO | WO 92/04310 | 3/1992 |
| WO | WO 95/07699 A1 | 3/1995 |
| WO | WO 98/20917 A2 | 5/1998 |
| WO | WO 01/05415 | 1/2001 |

(Continued)

OTHER PUBLICATIONS

US 6,214,374, 04/2001, Schmirler et al. (withdrawn)
Tamoxifen Citrate. Drug Facts and Comparisons, 2002, p. 2072.*
Tamoxifen Citrate, Dru Facts and Comparisions, 202, p. 2072.*
Bachmann et al. "Diagnosis and Treatment of Atrophic Vaginitis", American Family Physician, 61(10), 2000.*

(Continued)

*Primary Examiner* — Melissa Javier
(74) *Attorney, Agent, or Firm* — Marianne Fuierer; Moore & Van Allen, PLLC

(57) ABSTRACT

The present invention provides novel pharmaceutical compositions containing triphenylethylene derivative compounds, and methods of using the composition for treatment of symptoms associated with atrophic vaginitis. The pharmaceutical compositions are prepared for the vaginal administration of triphenylethylene derivative compounds in single or combination therapies. Preferably, the triphenylethylene derivative is tamoxifen.

15 Claims, No Drawings

(56) References Cited

U.S. PATENT DOCUMENTS

| | | |
|---|---|---|
| 2004/0157812 A1 | 8/2004 | Labrie |
| 2004/0191276 A1 | 9/2004 | Muni |
| 2004/0192598 A1 | 9/2004 | Kragie |
| 2004/0198706 A1 | 10/2004 | Carrara et al. |
| 2005/0118272 A1 | 6/2005 | Besse et al. |
| 2005/0143359 A1 | 6/2005 | Bell et al. |
| 2005/0182105 A1 | 8/2005 | Nirschl et al. |
| 2005/0187267 A1 | 8/2005 | Hamann et al. |
| 2005/0192310 A1 | 9/2005 | Gavai et al. |
| 2005/0209209 A1 | 9/2005 | Koch et al. |
| 2005/0215592 A1 | 9/2005 | Day et al. |
| 2005/0222100 A1 | 10/2005 | Kloosterboer et al. |
| 2005/0245539 A1 | 11/2005 | Mendla et al. |
| 2005/0250753 A1 | 11/2005 | Fink et al. |
| 2006/0018937 A1 | 1/2006 | Friedman et al. |
| 2006/0135619 A1 | 6/2006 | Kick et al. |
| 2006/0183724 A1 | 8/2006 | Diliberti et al. |
| 2006/0240111 A1 | 10/2006 | Fernandez et al. |
| 2006/0280797 A1 | 12/2006 | Shoichet et al. |
| 2007/0004693 A1 | 1/2007 | Woolfson et al. |
| 2007/0004694 A1 | 1/2007 | Woolfson et al. |
| 2007/0060589 A1 | 3/2007 | Purandare et al. |
| 2007/0111971 A1 | 5/2007 | Eaddy et al. |
| 2007/0270394 A1 | 11/2007 | El-Alfy et al. |
| 2008/0103155 A1 | 5/2008 | Mendla et al. |
| 2008/0132476 A1 | 6/2008 | Kosemund et al. |
| 2008/0234199 A1 | 9/2008 | Katamreddy et al. |
| 2008/0255078 A1 | 10/2008 | Katamreddy |
| 2008/0255089 A1 | 10/2008 | Katamreddy |
| 2008/0306036 A1 | 12/2008 | Katamreddy |
| 2008/0319078 A1 | 12/2008 | Katamreddy |
| 2009/0054383 A1 | 2/2009 | Labrie |
| 2009/0062374 A1 | 3/2009 | Czarnik |

FOREIGN PATENT DOCUMENTS

| | | |
|---|---|---|
| WO | WO 01/24772 A1 | 4/2001 |
| WO | WO 01/27127 | 4/2001 |
| WO | WO 01/54699 | 8/2001 |
| WO | WO 02/17929 | 3/2002 |
| WO | WO 02/078682 | 10/2002 |
| WO | WO 02/092102 | 11/2002 |
| WO | WO 02/094303 | 11/2002 |
| WO | WO 03/017974 | 3/2003 |
| WO | WO 03/039524 | 5/2003 |
| WO | WO 03/063859 | 8/2003 |
| WO | WO 03/084549 A1 | 10/2003 |
| WO | WO 03/097069 A1 | 11/2003 |
| WO | WO 03/097071 A1 | 11/2003 |
| WO | WO 03/103649 | 12/2003 |
| WO | WO 2004/052336 A3 | 6/2004 |
| WO | WO 2004/096151 A2 | 11/2004 |
| WO | WO 2005/016321 | 2/2005 |
| WO | WO 2005/033056 | 4/2005 |
| WO | WO 2005/084295 | 9/2005 |
| WO | WO 2005/084296 | 9/2005 |
| WO | WO 2006/023496 A2 | 3/2006 |
| WO | WO 2006/042021 A2 | 4/2006 |
| WO | WO 2006/114702 | 11/2006 |
| WO | WO 2006/127871 | 11/2006 |
| WO | WO 2007/062067 | 5/2007 |
| WO | WO 2007/062145 | 5/2007 |
| WO | WO 2007/062148 | 5/2007 |
| WO | WO 2007/062151 | 5/2007 |
| WO | WO 2007/062190 | 5/2007 |
| WO | WO 2007/118205 | 10/2007 |
| WO | WO 2008/067086 | 6/2008 |
| WO | WO 2009/021323 | 2/2009 |

OTHER PUBLICATIONS

"Commercially Available Hormones," http://www.goodpharma.com/prescription%20hormones.htm, retrieved Oct. 21, 2004.

"Current Drugs Available for HRT/ERT," Doctors Against Premarin, Copyright 2002, http://www.doctorsagainstpremarin.org/hrt_carts.htm, retrieved Oct. 21, 2004.

Dugal, et al., 2000, "Comparison of usefulness of estradiol vaginal tablets and estriol vagitories for treatment of vaginal atrophy," *Acta Obstet Gynecol Scand*, vol. 79: p. 293-297.

The Writing Group for the PEPI Trial, 1996, "Effects of Hormone Replacement Therapy on Endometrial Histology in Postmenopausal Women," *JAMA*, vol. 275, No. 5: p. 370-375.

"Estradiol (vaginal)," http://store.yahoo.com/egeneralmedical/rxlist00000900.html eGeneralMedical Incorporation, Copyright 2000, retrieved Oct. 21, 2004.

"Estro-All Natural Estrogen Cream with Natural Porgesterone," http://www.heranswer.com/estro.asp, retrieved Oct. 21, 2004, Copyright Rose Enterprises.

Elkind-Hirsch, et al., 2002, "Sequential hormonal supplementation with vaginal estradiol and progesterone gel corrects the effect of clomiphene on the endometrium in oligo-ovulatory women." *Hum Reprod*, vol. 17, No. 2: p. 295-8 (abstract only, Medscape from WebMD: http//intapp.medscape.com).

Ferrero, et al., 2002, "Vaginal micronized progesterone in continuous hormone replacement therapy. A prospective randomized study," *Minerva Ginecol*, vol. 54, No. 6: p. 519-30 (abstract only, Medscape from WebMD: http//intapp.medscape.com).

Follingstad, 1978, "Estriol, the Forgotten Estrogen?" *JAMA*, vol. 239, No. 1: p. 29-30.

Gambrell, 2003, "Progesterone skin cream and measurements of absorption," *Meaopause*, vol. 10, No. 1: p. 1-3 (abstract only, Medscape from WebMD: http//intapp.medscape.com).

"Genitourinary Tract Changes," Oct. 2004, vol. 104, No. 4 (Supplement), *The American College of Obstetricians and Gynecologists*, Published by Lippincott Williams & Wilkins.

Head, 1998, "Estriol: Safety and Efficacy," *Alternative Medicine Review*, vol. 3, No. 2: p. 101-113.

Iosif, 1992, "Effects of portracted administration of estriol on the lower genito urinary tract in postmenopausal women," *Arch Gynecol Obstet*, vol. 251: p. 115-120.

Kendall, et al., 2006, "Caution: Vaginal estradiol appears to be contraindicated in postmenopausal women on adjuvant aromatase inhibitors," *Anals of Oncology*, vol. 17: p. 584-587.

Kim, et al., 2006, "Effects of tamoxifen on vaginal blood flow and epithelial morphology in the rat," *BMC Womens Health*, vol. 6: p. 14.

Kuhl, 1990, "Pharmacokinetics of oestrogens and progestogens," *Maturitas*, vol. 12: p. 171-197.

Leonetti, et al., 2003, "Topical progesterone cream has an antiproliferative effect on estrogen-stimulated endometrium," *Fertil Steril*, vol. 79, No. 1: p. 221-2 (abstract only, Medscape from WebMD: http//intapp.medscape.com).

Minkin and Giblin, "Manual of Management Counseling for the Perimenopausal and Menopausal Patient: A Clinician's Guide," the Parthenon Publishing Group, Copyright 2004: p. 80-81.

Miodrag, et al., 1991, "Tamoxifen and partial oestrogen agonism in postmenopausal women," *Age and Ageing*, vol. 20: p. 52-54.

Raz and Stamm, 1993, "A controlled trial of intravaginal estriol in postmenopausal women with recurrent urinary tract infections," *The New England Journal of Medicine*, vol. 329, No. 11: p. 753-756.

Silfen, et al., 1999, "Selective estrogen receptor modulators: tissue selectivity and differential uterine effects," *Climacteric*, vol. 2: p. 268-283.

U.S. Department of Health and Human Services Food and Drug Administration Center for Drug Evaluation and Research (CDER), "Guidance for Industry: Estrogen and Estrogen/Progestin Drug Products to Treat Vasocmotor Symptoms and Vulvar and Vaginal Atrophy Sysmptoms—Recommendations for Clinicla Evaluation," Rockville, Maryland, Jan. 2003.

Vassillos, et al., 1978, "Estriol in the management of the menopause," *JAMA*, vol. 239, No. 16: p. 1638-1641.

Yang, et al., 1995, "Efficacy and saftey of estriol replacement therapy for climacteric women," *Chin Med J*, vol. 55: p. 386-91.

Zhang, et al., 2005, "The molecular basis of tamoxifen inductioin of mouse uterine epithelial cell proliferation," *Journal of Endocrinology*, vol. 184: p. 129-140.

(56) References Cited

OTHER PUBLICATIONS

D. Grady, "Management of Menopausal Symptoms," New Engl J Med, v 355 n22, 2338-47 (Nov. 30, 2006).
J. Dew et al., "A cohort study of topical vaginal estrogen therapy in women previously treated for breast cancer," Climacteric, v6, n1, 45-52 (Mar. 2003).
B. Kessel et al., "Effect of raloxifene on sexual function in postmenopausal women," Climacteric, v6 n3, 248-256 (Sep. 2003).
P. Sukumvanich et al., "Current issues regarding tamoxifen and the genital tract: a review," Women's Oncology Review, v4 n2, 85-94 (Jun. 2004).
M. Seoud et al., "Gynecologic tumors in tamoxifen-treated women with breast cancer," Obstet Gynecol, v82 n2, 165-169 (Aug. 1993).
Alexandersen, et al., 2001, "Efficacy of Levormeloxifene in the Prevention of Postmenopausal Bone Loss and on the Lipid Profile Compared to Low Dose Hormone Replacement Therapy," *The Journal of Clinical Endocrinology & Metabolism*, vol. 86, No. 2: p. 755-760.
Baessler, et al., 2008, "An interviewer-administered validated female pelvic floor questionnaire for community-based research," *Menopause: The Journal of The North American Menopause Society*, vol. 15, No. 5: p. 973-977.
Cella, et al., 2006, "Quality of life of postmenopausal women in the ATAC ("Arimides", tamoxifen, alone or in combination) trial after completion of 5 years' adjuvant treatment for early breast cancer," *Breast Cancer Res Treat*, vol. 100: p. 273-284.
Cheng, et al., 1997, "Comparison of Endometrial Changes among Symptomatic Tamoxifen-Treated and Nontreated Premenopausal and Postmenopausal Breast Cancer Patients," *Gynocologic Oncology*, vol. 66: p. 233-237.
Christgau, et al., 2004, "Suppression of elevated cartilage turnover in postmenopausal women and in ovariectomized rats by estrogen and selective estrogen-receptor modulator (SERM)," *Menopause: The Journal of the North American Menopause Society*, vol. 11, No. 5: p. 508-518.
Cohen, et al., 1999, "Endometrial pathology in postmenopausal tamoxifen treatment: comparison between gynaecologically symptomatic and asymtomatic breast cancer patients," *J. Clin. Pathol.*, vol. 52: p. 278-282.
Crandall, et al., 2004, "Association of breast cancer and its therapy with menopause-related symptoms," *Menopause: The Journal of the North American Menopause Society*, vol. 11, No. 5: p. 519-530.
Derzko, et al., 2007, "Management of sexual dysfunction in postmenopausal breast cancer patients taking adjuvant aromatase inhibitor therapy," *Current Oncology*, vol. 14, Suppl. I: p. S20-S40.
Dessole, et al., 2004, "Efficacy of low-dose intravaginal estriol on urogenital aging in postmenopausal women," Menopause: *The Journal of the North American Menopause Society*, vol. 11, No. 1: p. 49-56.
Dugal, et al., 2000, "Comparison of usefulness of estradiol vaginal tablets and estriol vagitories for treatment of vaginal atrophy," *Acta Obstet Gyencol Scand*, vol. 79: p. 293-297.
Ettinger, et al., 2008, "Measuring symptom relief in studies of vaginal and vulvar atrophy: the most bothersome symptom approach," *Menopause: The Journal of the North American Menopause Society*, vol. 15, No. 5: p. 885-889.
Ellmen, et al., 2003, "Estrogenic effects of toremifene and tamoxifen in postmenopausal breast cancer patients," *Breast Cancer Research and Treatment*, vol. 82: p. 103-111.
Foidart, et al., 1991, "Efficacy of sustained-release vaginal oestriol in alleviating urogenital and systemic climacteric complaints," *Maturitas*, vol. 13: pp. 99-107.
Gallicchio, et al., 2004, "Association of tamoxifen (TAM) and TAM metabolic concentrations with self-reported side effects of TAM in women with breast cancer," Breast Cancer Research and Treatment, vol. 85: p. 89-97.
Ganz, et al., 2001, "Impact of Tamoxifen Adjuvant Therapy on Symptoms Functioning, and Quality of Life," *Journal of the National Cancer Institute Monographs*, No. 30: p. 130-134.

Glaus, et al., 2006, "Fatigue and menopausal symptoms in women with breast cancer undergoing hormonal cancer treatment," *Annals of Oncology*, vol. 17, No. 5: p. 801-806.
Goldstein, et al., 2002, "Adverse events that are associated with the selective estrogen receptor modulator levormeloxifene in an aborted phase III osteoporosis treatment study," *American Journal of Obstetrics and Gynecology*, vol. 187, No. 3: p. 521-527.
Graham, et al., 1997, "Physiological Action of Progesterone in Target Tissues," *Endocrine Reviews*, vol. 18, No. 4: p. 502-519.
Gruber, et al., 2002, "Production and Actions of Estrogens," *The New England Journal of Medicine*, vol. 346, No. 5: p. 340-352.
Kendall, et al., 2006, "Caution: Vaginal estradiol appears to be contraindicated in postmenopausal women on adjuvant aromatase inhibitors," *Annals of Onocology*, vol. 17: p. 584-587.
Kim, et al., 2006, "Effects of tamoxifen on vaginal blood flow and epithelial morphology in the rat," *BMC Women's Health*, vol. 6, No. 14: p. 1-16.
Lahti, et al., 1994, "Maturation of Vaginal and Endometrial Epithelium in Postmenopausal Breast Cancer Patients Receiving Long-Term Tamoxifen," *Gynecologic Oncology*, vol. 55: p. 410-414.
NAMS (North American Menopause Society) "Menopause e-Consult", Apr. 2008, vol. 4, Issue 2.
NAMS (North American Menopause Society) Position Statement, 2008, "Estrogen and progestogen use in postmenopausal women: Jul. 2008 position statement of the North American Menopause Society," *Menopause: The Journal of the North American Menopause Society*, vol. 15, No. 4: p. 584-602.
NICE clincical guideline 40, Developed by the National Collaborating Centre for Women's and Children's Health, Oct. 2006, "Urinary incontinence: The management of urinary incontinence in women," *NHS* (*National Institute for Health and Clinical Excellence*): p. 1-36.
Ozyazici, et al., 2003, "In-vitro Evaluation and Vaginal Absorption of Metronidazole Suppositories in Rabbits," *Journal of Drug Targeting*, vol. 11, No. 3: p. 177-185.
Pathak, et al., 1996, "Activation of 4-hydroxytamoxifen and the tamoxifen derivative metabolite E by uterine peroxidase to form DNA adducts: Comparison with DNA adducts formed in the unterus of Sprague-Dawley rats treated with tamoxifen," *Carcinogenesis*, vol. 17, No. 9: p. 1785-1790.
Ravn, et al., 2006, "What can be learned from the levormeloxifene experience?" *Acta Obstetricia et Gynecologica*, vol. 85: p. 135-142.
Rizk, et al., 2001, "Evidence of Progesterone Receptors in the Mucosa of the Urinary Bladder," *Scand J Urol Nephrol*, vol. 35: p. 305-309.
Shiota, et al., 2002, "Reciprocal Effects of Tamoxifen on Hormonal Cytology in Postmenopausal Women," *Acta Cytologica*, vol. 46, No. 3: p. 499-506.
Skrumsager, et al., 2002, "Levormeloxifene: safety, pharmacodynamics and pharmacokinetics in healthy postmenopausal women following single and multiple doses of a new selective oestrogen receptor modulator," *J. Clin.Pharmacol.*, vol. 53: p. 284-295.
Swift, et al., 1993, "Effects of Progesterone on the Urinary Tract," *Int Urogynecol J*, vol. 4: p. 232-236.
Trinkaus, et al., 2008, "Should Urogenital Atrophy in Breast Cancer Survivors Be Treated with Topical Estrogens?" *The Oncologist*, vol. 13: p. 222-231.
Van Haaften, et al., 1997, "Biochemical and histological effects of vaginal estriol and estradiol applications on the endometrium, myometrium and vagina of postmenopausal women," *Gynecol. Endocrinol.*, vol. 11: p. 175-185.
Vardy, et al., 2003, "Short-term urogenital effects of raloxifene, tamoxifen, and estrogen," *Am J Obstet Gynecol*, vol. 189, No. 1: p. 81-88.
Villanueva, et al., 1981, "Intravaginal Administration of Progesterone: Enhanced Absorption After Estrogen Treatment," *Fertility and Sterility*, vol. 35, No. 4: p. 433-437.
Vooijs, et al., 1995, "Review of the endometrial safety during intravaginal treatment with estriol," *European Journal of Obstetrics & Gynecology and Reproductive Biology*, vol. 62: p. 101-106.

(56) References Cited

OTHER PUBLICATIONS

Yildirim, et al., 2007, "The Effect of Long-Term Tamoxifen Usage on the Lower Part of Female Genital Tract in Breast Cancer Survivors: A Review," Marmara Medicl Journal, vol. 20, No. 3: p. 196-201.
Zullo, et al., 2005, "Vaginal estrogen therapy and overactive bladder symptoms in postmenopausal patients after a tension-free vaginal tape procedure: a radnomized clinical trial," Menopause: The Journal of the North American Menopause Society, vol. 12, No. 4: p. 421-427.
Chinese Office Action, corresponding to Chinese Patent Application No. 200780027066.8, issued on Sep. 13, 2012.
Australian Office Action, issued by the Australian Patent Office for corresponding Australian Patent Application No. 2007256718, dated Feb. 16, 2012.
Weismiller, D.G., Menopause, Primary Care—Clinics in Office Practice, 36/1: 199-226 (Mar. 1, 2009).
Castelo-Branco, C.; Cancelo, M.J., "Compounds for the treatment of atrophic vaginitis," Expert Opinion on Therapeutic Patents (United Kingdom), 18/12: 1385-1394 (Dec. 1, 2008).
Komm, Barry S., "A new approach to menopausal therapy: the tissue selective estrogen complex," Women's Health and Musculoskeletal Biology Research, Reproductive Sciences (Thousand Oaks, Calif.), 15(10): 984-92 (Dec. 2008).
Stovall, D.W.; Pinkerton, J.A.V., "Estrogen agonists/antagonists in combination with estrogen for prevention and treatment of menopause-associated signs and symptoms," Women's Health (Women's Health) (United Kingdom), 4/3: 257-268 (May 1, 2008).
Nijland, E.A. et al., "Effects of tibolone and raloxifene on health-related quality of life and sexual-function," Maturitas, 58(2): 164-173 (Oct. 20, 2007).
Castelo-Branco, C.; Rostro, F., "Management of menopause," Minerva Ginecologica (Italy), 58/2: 137-152 (Apr. 1, 2006).
Fraser, I.S.; Mansour, D., "Delivery systems for hormone replacement therapy," Expert Opinion on Drug Delivery (United Kingdom), 3/2: 191-204 (Mar. 1, 2006).
Ponzone, et al., "Vaginal oestrogen therapy after breast cancer: Is it safe?" European Journal of Cancer (United Kingdom), 41/17 (2673-2681) (Nov. 1, 2005).
Ballagh, "Vaginal hormone therapy for urogenital and menopausal symptoms," Seminars in Reproductive Medicine (Semin. Reprod. Med.) (United States), 23/2: 126-140 (May 1, 2005).
Ospemifene. Treatment of postmenopausal syndrome treatment of osteoporosis selective estrogen receptor modulator, Sorbera, L.A. (Reprint); Castaner, J; Bayes, M., Drugs of the Future, 29(1): 38-44 (Jan. 2004).
Sitruk-Ware, "Alternatives for optimal hormone replacement therapy," Climacteric (United Kingdom), 6/Suppl. 2: 11-16 (Aug. 1, 2003).
Rauthe, et al, "Treatment of menopausal symptoms in women with breast cancer," Internistische Praxis (Germany), 43/2: 295-300 (Jun. 1, 2003).
Robinson and Cardozo, "Urogenital effects of hormone therapy," Best Practice and Research in Clinical Endocrinology and Metabolism (United Kingdom ), 17/1: 91-104 (Mar. 1, 2003).
Kovalevsky, "Female sexual dysfunction and use of hormone therapy in postmenopausal women," Seminars in Reproductive Medicine, 23(2): 180-187 (May 5, 2005).
Pinkerton and Santen, "Use of alternatives to estrogen for treatment of menopause," Minerva Endocrinologica (Italy), 27(1): 21-41 (Mar. 2002).
Trinkaus, et al, "Should Urogenital Atrophy in Breast Cancer Survivors Be Treated with Topical Estrogens?", The Oncologist (United States) 13:222-231 (Mar. 2008).
Menopause pharmacotherapeutic development—CBI's second annual conference, Portman, D., IDrugs (United Kingdom), pp. 178-18 (Mar. 1, 2007).
16th Annual meeting of the North American Menopause Society, Prescott, L.M.; Prescott, S.L., Pa nd T ( P T ) (United States), 30/12: 736-739 (Dec. 1, 2005).
Geisthovell and Rabe, "Individualized therapeutic strategies of menopausal transition, and peri-/postmenopause—Update 2002," Reproduktionsmedizin (Germany), 18/5: 247-268 (Dec. 1, 2002).
Bachmann and Nevadunsky, "Diagnosis and treatment of atrophic vaginitis," American Family Physician, 61/10: 3090-3096 (May 15, 2000).
Pritchard, "The role of hormone replacement therapy in women with a previous diagnosis of breast cancer and a review of possible alternatives," Annals of Oncology—Official Journal of the European Society for Medical Oncology (Netherlands), 12(3): 301-10 (Mar. 2001).
Hormone replacement therapy and beyond: The clinical challenge of menopausal symptoms in breast cancer survivors, Geriatrics, vol. 57, No. 9, pp. 25-31 (Sep. 2002).
ACOG Practice Bulletin No. 39, Oct. 2002. Selective estrogen receptor modulators, International Journal of Gynecology and Obstetrics, 79/3: 289-298 (Dec. 1, 2002).
Selective estrogen receptor modulators, Obstetrics and Gynecology, 100/4: 835-844 (Oct. 1, 2002).
Adverse events reported by postmenopausal women in controlled trials with raloxifene, Obstetrics & Gynecology, vol. 93, No. 4, pp. 558-565 (Apr. 16, 1999).
Waldman, "Menopause: When hormone replacement therapy is not an option: Part II," Journal of Women's Health, 7/6: 673-683 (Aug. 1, 1998 ).
Wren, "The management of urogenital atrophy following genital tract cancer," International Urogynecology Journal and Pelvic Floor Dysfunction, 6/2 (61-62) (Jul. 26, 1995).
Pinkerton and Santen, "Alternatives to the use of estrogen in postmenopausal women," Endocrine Reviews, 20(3): 308-320 (Jun. 1999).
"Different Forms of HRT: Estrace, Gynodiol," Feb. 9, 2004, EarlyMenopause.com, pp. 1-4.
Gibbs, "Estrogen Replacement Enhances Acquisition of a Spatial Memory Task and Reduces Deficits Associated with Hippocampal Muscarinic Receptor Inhibition," Hormones and Behavior. (1999);36:222-233.
Jelovsek, "Progesterone—Its Uses and Effects," Apr. 4, 2004, Woman's Diagnostic Cyber, pp. 1-6.
Lee et al., "Estriol: a Safer Replacement Estrogen", What Your Doctor May Not Tell You About Breast Cancer, pp. Table of contents, 97-170, 196-207, and 432-442 (Index) (Warner Wellness Books 2002).
Lee et al.., What your Doctor May Not Tell You About Menopause, pp. Table of contents, 34-49, 67-97, 123-134, 244-245, 256-257, 284-288, 323-325, and Index (Warner Wellness Books 2004).
Luisi et al., "A group-comparative study of effects of ovestin cream versus premarin cream in post-menopausal women with vaginal atrophy," Maturitas (1980); 2: 311-319.
Lyytinen et al. "Breast Cancer Risk in Postmenopausal Women Using Estrogen-Only Therapy", Obstetrics & Gynecology (2006); 108(6): 1354-1360.
Minkin and Giblin, "Manual of Management Counseling for the Perimenopausal and Menopausal Patient, A Clinician's Guide," pp. Table of contents, 36-42, 78-81, and 102-104 (Index) (Parthenon Publishing 2004).
Molander et al., "Effect of oral oestriol on vaginal flora and cytology and urogenital symptoms in the post-menopause," Maturitas (1990); 12:113-120.
Ratner et al., "Menopause and Hormone Replacement Therapy," Western Journal of Medicine (2001); 175: 32-34.
Samsioe et al., "Occurrence, nature and treatment of urinary incontinence in a 70-year-old female population," Maturitas (1985); 7: 335-342.
Literature search results, May 6, 2009.
Petition Under 37 CFR 1.47(a), accompanied with a declaration by Bernadette Klamerus and a declaration by Wayne Kennard, filed in U.S. Appl. No. 12/163,334, dated Nov. 24, 2008, 12 pages total.

\* cited by examiner

METHOD OF TREATING ATROPHIC VAGINITIS

CROSS-REFERENCE TO RELATED APPLICATIONS

This application claims priority under 35 U.S.C. §119, based on U.S. Provisional Application Ser. Nos. 60/810,715, filed Jun. 2, 2006, and 60/917,800, filed May 14, 2007. The teachings of these referenced applications are incorporated herein by reference in their entirety.

FIELD OF THE INVENTION

The present invention relates to using triphenylethylene derivative compounds in a novel pharmaceutical composition for vaginal therapy for the treatment of symptoms associated with atrophic vaginitis.

BACKGROUND OF THE INVENTION

Atrophic vaginitis is a hormone-dependent disease involving the lower urinary tract, genital tract, and pelvic floor. Generally, atrophic vaginitis becomes evident during or after menopause, the symptoms increasing with age. Symptoms relating to urogenital aging are due to estrogen loss from follicular depletion in the menopausal ovary. This estrogen loss accounts for the majority of the anatomical, cytological, bacteriologic, and physiologic genital changes that occur in the vagina.

With estrogen loss, the vagina shortens, narrows, and the vaginal walls become thinner, less elastic and pale in color. As a result, numerous symptoms begin to appear. Collectively, the vaginal symptom complex is referred to as atrophic vaginitis. Unlike vasomotor symptoms, atrophy-related problems such as dyspareunia, burning and chronic vaginitis do not disappear with time. Irritation and burning are frequently a result of a chronic discharge caused by pH elevations and bacteriologic changes of the vaginal vault. Itching, which often interferes with a restful sleep, is also due to thinning and inflammation of the vulvovaginal epithelial layer. The vaginal surface thus becomes friable, with petechiae, ulcerations, and bleeding often occurring after minimal trauma.

The most common vaginal atrophy symptom is vaginal dryness. A survey of 1,200 Swedish menopausal women randomly selected from a birth cohort indicated that half reported some type of vaginal or urogenital symptom, the most common being vaginal dryness and associated dyspareunia (Iosif et al., *Acta Obstetricia et Gynaecologica Scandinnavica* 1984; 63: 257-60). Vaginal dryness can be bothersome to sexually abstinent women, but it is voiced as the most bothersome problem in sexually active women who find coital activity uncomfortable because of inadequate lubrication (Bachmann et al., *Maturitas* 1984; 6: 19-29). Vaginal dryness has not only been associated with painful intercourse, but also a decrease in libido (Bachmann et al., *Maturitas* 1985; 7: 211-216). Vaginal dryness is not limited to menopausal women; up to 15% of women who are still menstruating also report dyspareunia and dryness (Oldenhave, Well-Being and Sexuality in the Climacteric: A Survey Based on 6,622 Women [dissertation]. Leidshendam, United Kingdom: Excelsior; 1991).

It has been suggested that about 50% of otherwise healthy women over 60 years of age have symptoms related to vaginal atrophy (Iosif et al., *Acta Obstetricia et Gynaecologica Scandinnavica* 1984; 63: 257-60). Overall, in about 45% of menopausal women vaginal atrophy can be clinically manifest as a syndrome of vaginal dryness, itching, irritation and dyspareunia (Bygdeman et al., *Maturitas* 1996; 23: 259-63). The vaginal symptoms range in severity from annoying to debilitating. In the United States, 20 million women, who do not undergo estrogen hormone therapy, will have socially disabling symptoms related to urogenital atrophy (Samsioe, *Am J Obstet Gynecol* 1998; 178: S245-S249).

Estrogen replacement therapy has been for many years the basis of drug therapy for the maintenance of menopausal urogenital health. However, it is well known that estrogen induces cell proliferation in mammary gland epithelium (Jordon, V C, *Scientific American* 1998: 60-67). Notably, as early as 12 months, the percentage of women with density grade increases was 0% in the placebo group and 3.5% in the estrogen alone group (Greendale G A et al., *Ann Intern Med* 1999; 130: 262-9). Overall, estrogen has long been implicated as the main sex hormone in the initiation and promotion of breast cancer. The case against estrogen has been well documented (Hulka et al. *Lancet* 1995, 346: 883-997; Early breast cancer trialists collaborative group, *Lancet* 1992; ii: 1-15; Early breast cancer trialists collaborative group, *Lancet* 1992, ii: 71-85; Haddow et al., *British Medical Journal* 1944 (September 23): 4368-4373; Henderson et al., *Cancer Research* 1988, 48: 246-253).

In contrast, continuous large doses of progesterones have been shown to be as effective as tamoxifen when given to women with advanced breast cancer (Rose et al., *Hormone Research* 1989, 32 (Suppl 1): 189-197). Progesterone appears to have no effect on quiescent breast cells (Clark et al., *Endocrinology Reviews* 1990, 11(2): 266-301). Progesterone has also been shown to inhibit the production of cathepsin-D, a protein that is mitogenic and could play a role in tumor invasion (Clark et al., *Endocrinology Reviews* 1990; 11(2): 266-301).

Removal of the ovaries or administration of an anti-estrogenic drug has been a major therapeutic option in breast cancer-risk patients. The removal of estrogen has a negative impact on a women's health, increasing the risk for osteoporosis and impeding urogenital health. For women after treatment of breast cancer, menopausal symptoms will be so severe that consideration must be given to using some form of hormonal therapy. Thus, the search for menopausal therapies, which preserve estrogen's potential benefits while avoiding undesirable estrogen effects in breast tissue, has led to the development of compounds known as selective estrogen receptor modulators (SERMs). The SERMs represent a structurally diverse group of non-steroidal compounds that can evoke either estrogen-like (agonist) or estrogen-blocking (antagonist) responses that vary by cell type and tissue.

The most successful SERM to date is tamoxifen (available commercially from Astra-Zeneca as Nolvadex®), which is a triphenylethylene derivative. Tamoxifen demonstrates antiestrogenic effects through its ability to compete with estrogen for binding sites in target tissue such as breast tissue (Fisher et al., *N Engl J Med* 1989; 320: 479-84). Tamoxifen is widely used for the treatment of hormone-responsive breast cancer (Osborne C K, *N Engl J Med* 1998; 339: 1609-18). Specifically, tamoxifen is indicated for the treatment of metastatic breast cancer, for the use of adjuvant therapy for the treatment of localized breast cancer, and for the reduction of risk of breast cancer in high-risk women (Mitlak et al., *Drugs* 1999; 57: 653-663).

Tamoxifen has been shown to act as an agonist in uterine tissue (Barakat R R, *Cancer Treat Res* 1998; 94: 195-207). Tamoxifen stimulates uterine epithelial cell proliferation, increasing the risk of uterine cancer four-fold in women over 50 years of age, thus limiting its utility in treating healthy postmenopausal women (Fisher et al., *J Natl Cancer Inst* 1998; 90: 1371-88). Since, uterine safety is of concern to women who are considering therapy for breast cancer, the use of tamoxifen has been cautioned in non-hysterectomized patients. Overall, the ACOG continues to recommend concomitant progestin for women receiving an estrogen agonist regimen (American College of Obstetricians and Gynecologists, Hormone replacement therapy. ACOG technical bulletin no. 93. Washington, D.C.: American College of Obstetricians and Gynecologists, 1992). The Food and Drug Administration (FDA) has imposed a black box warning on all FDA approved unopposed estrogens stating the following: "The use of unopposed estrogens in women who have a uterus is associated with an increased risk of endometrial cancer." The FDA has imposed a similar black box warning on tamoxifen with regards to the increased risk of endometrial cancer.

The mechanism by which SERMs can exert both estrogen agonist and estrogen antagonist effects in a tissue-selective manner is not completely understood, but recent advances in this field have shed much light on this complex issue. Both estrogens and SERMs regulate genes through a series of molecular events that occur subsequent to their binding the intracellular estrogen receptor (Siris et al., Selective estrogen receptor modulators. *The Aging Skeleton*. San Diego, Calif.: Academic Press, 1999, Ch 42: 507-20). There are two types of estrogen receptors that have been identified to date: ER-alpha and ER-beta. Both types of estrogen receptors have two transcriptional activation domains, Activation Factor-1 (AF-1) and Activation Factor-2 (AF-2). Activation of a domain will regulate the level of DNA transcriptional activity. For example, tamoxifen will bind to uterine ER-alpha and stimulate AF-1 activity, but AF-2 activity is inhibited (Smith et al., *Molecular* Endocrinology 1997; 11: 657-666; McDonnell D., *Trends in Endocrinology and Metabolism* 1999; 10: 301-311). Further, the action of tamoxifen upon cell cycle machinery in the uterine epithelium is similar to that observed upon estradiol stimulation; tamoxifen induces a wave of DNA synthesis in uterine epithelial with kinetics similar to those seen after estradiol treatment (Hart J E, *Pharmacol Ther.* 1990; 47: 203-18). The AF-1 transcriptional activation domain of the estrogen receptor that is activated both by estradiol and tamoxifen binding to this receptor regulates the response seen in the uterus (Zhang et al., *Journal of Endocrinology* 2005; 184: 129-140).

Both ER-alpha and ER-beta are found in the vaginal epithelium. The expression of ER-alpha, and not ER-beta, in menopausal women has been regulated by estrogen replacement therapy. In menopausal patients, ER-alpha has been detected significantly more frequently in the vaginal walls of estrogen treated patients than in those who were untreated (Rezapour et al., *Int Urogyncol J Pelvic Floor Dysfunct* 2003; 14 (4): 276-81). Specifically, ER-alpha was detected in the vaginal epithelial, stromal and smooth muscle cells, but was not observed in vaginal blood vessels. ER-beta was detected in epithelial and vascular smooth muscle cells of the vagina. Expression of ER-beta markedly declines in menopause, regardless of estrogen replacement therapy (Gebhart J B et al., *Am J Obstste Gynecol* 2001; 185: 1325-30).

There is currently only one approved method for the treatment of atrophic vaginitis, and that is the administration of exogenous estrogens. Further, FDA guidance states that vaginal products should be considered for the treatment of symptoms of vulvar and vaginal atrophy associated with the menopause when prescribing solely for the treatment of symptoms of vulvar and vaginal atrophy (See Guidance For Industry: Labeling Guidance for Noncontraceptive Estrogen Drug Products for the Treatment of Vasomotor Symptoms and Vulvar and Vaginal Atrophy Symptoms—Prescribing Information for Health Care Providers and Labeling, available at http://www.fda.gov/cder/guidance/index.htm). Yet, the FDA has imposed a warning on all FDA approved estrogens stating the following:

(Trade name) should not be used in women with any of the following conditions: known, suspected, or history of cancer of the breast.

(See Guidance For Industry: Labeling Guidance for Noncontraceptive Estrogen Drug Products for the Treatment of Vasomotor Symptoms and Vulvar and Vaginal Atrophy Symptoms—Prescribing Information for Health Care Providers and Labeling, available at http://www.fda.gov/cder/guidance/index.htm). Overall, many women fear the increase risk of developing breast cancer with estrogen replacement therapy. Thus, while estrogen therapy is effective in treating atrophic vaginitis, there is poor patient compliance. Furthermore, there is no approved method for the treatment of atrophic vaginitis in breast cancer risk patients. There is no approved vaginal administered method for the treatment of atrophic vaginitis with the use of triphenylethylene derivatives. There is no approved vaginal administered method for the treatment of atrophic vaginitis with the use of triphenylethylene derivatives in combination with progesterone to be used in non-hysterectomized women.

Thus, there is a clear need in the art to provide an effective and safe vaginally administered therapy to treat atrophic vaginitis in women who are unable or unwilling to take estrogen therapy due to increased breast cancer or other carcinogenic risk. Overall, a new method that would have the benefits of estrogens, and at the same time decrease the carcinogenic risks and side effects, is needed because the present methods are far from optimal. No drug candidate has emerged to fill the needs of women who have increased carcinogenic risks and who require the benefits of estrogen replacement to live productive lives.

SUMMARY OF THE INVENTION

The present invention relates to a pharmaceutical composition that is effective in the treatment of symptoms associated with atrophic vaginitis.

In one embodiment of the invention, the pharmaceutical composition includes a therapeutically effective amount of a SERM, preferably a triphenylethylene derivative compound, wherein the triphenylethylene derivative acts as a selective estrogen receptor modulator, and a therapeutically effective amount of a suitable carrier suitable for vaginal administration. In another embodiment, the pharmaceutical composition also includes a therapeutically effective amount of progesterone.

In one particular embodiment, the composition is prepared as a vaginal suppository. In another particular embodiment, the composition is prepared as a vaginal cream.

In one aspect of the invention, the triphenylethylene derivative compound is selected from the group consisting of 2-[4-(1,2-diphenyl-1-butenyl) phenoxy]-N, N-dimethyl-ethanamine 2-hydroxy-1,2,3-propanetricarboxylate (otherwise known as tamoxifen citrate), a stereoisomer thereof, a non-toxic pharmaceutical acceptable salt, and an ester thereof. In certain embodiments, the triphenylethylene derivative compound is present in an amount of from about 0.2 mg to about 200 mg per dose, preferably from about 2 mg to about 20 mg per dose.

In another aspect of the invention, the progesterone is micronized progesterone. In certain embodiments, the progesterone compound is present in an amount of from about 5.0 mg to about 500 mg per dose.

In one aspect of the invention, the pharmaceutical composition includes at least one constituent selected from the group consisting of additives, pharmaceutically acceptable carriers, fatty acid base, a preservative, a dye, a binder, a suspending agent, a dispersing agent, a colorant, a disintegrant, an excipient, a diluent, a lubricant, a plasticizer, oils, and mixtures thereof.

In particular embodiments, the triphenylethylene derivative compound is present in an amount effective to produce a tissue specific estrogenic effect. In other embodiments, the triphenylethylene derivative compound is present in an amount effective to reduce the incidence of thrombogenic events associated with a therapeutic oral dose. In other embodiments, the triphenylethylene derivative compound is present in an amount effective to reduce the incidence of a worsening of climacteric symptom associated with a therapeutic oral dose.

In another embodiment of the invention, the progesterone compound is present in an amount effective to produce an anti-proliferative effect on the endometrium by inhibiting endometrial proliferation.

In certain embodiments, the pharmaceutical composition also has a suspending agent, preferably micronized silica gel. In particular embodiments, the amount of micronized silica gel is from about 0.01 gm to about 0.1 gm per unit dose.

In another embodiment, the pharmaceutical composition also has a fatty acid base. In particular embodiments, the fatty acid base includes JAB base.

The present invention also provides for a method of treating symptoms of atrophic vaginitis, wherein the method includes vaginally administering an effective amount of a triphenylethylene derivative compound in hysterectomized patients. In one embodiment, the method includes vaginally administering a therapeutically effective amount of a triphenylethylene derivative compound and a progesterone compound in non-hysterectomized patients.

In one embodiment, the method modulates biological activity of a urogenital estrogen receptor by exposing the estrogen receptor to a triphenylethylene derivative compound. In a particular embodiment, the estrogen receptor is an alpha isoform. In one embodiment, the compound activates estrogen receptor alpha via an Activation Factor 1 domain.

In another embodiment of the invention, the therapeutically effective amount of the triphenylethylene derivative compound is effective to reduce the incidence of thrombogenic events associated with oral therapy. In a different embodiment, the therapeutically effective amount of the triphenylethylene derivative compound is effective to reduce the incidence of a worsening of climacteric symptom associated with a oral therapy. In yet another embodiment, the therapeutically effective amount of the progesterone is effective to reduce concomitant liability of adverse uterine effects associated with unopposed triphenylethylene derivative administration during menopause.

In a specific embodiment of the invention, about 20 mg tamoxifen citrate is combined with about 15 mg micronized progesterone, and the composition causes an antiproliferative effect on an endometrium. In another embodiment, about 10 mg tamoxifen citrate is combined with about 7.5 mg micronized progesterone, and in yet another embodiment, about 30 mg tamoxifen citrate is combined with about 30 mg micronized progesterone.

In particular embodiments, the composition is administered for at least 3 months, preferably for at least 12 months.

In other embodiments, the composition is administered vaginally at least one time per week, preferably at least two times per week.

These and other aspects of the invention are discussed more in the detailed description and examples.

DETAILED DESCRIPTION

The present invention advantageously provides for a method and a pharmaceutical composition in the treatment of symptoms associated with hormone deficient disorders responsive to estrogen, such as atrophic vaginitis. Moreover, the invention describes both a safe and clinically effective method to treat atrophic vaginitis resulting from surgical menopause, iatrogenic menopause, natural menopause and conditions leading to ovarian failure thus manifesting as menopause in women. The present invention provides a long-term treatment regimen, e.g., greater than three months of continuous treatment, up to greater than 60 months of continuous treatment, while minimizing and/or preventing health risks associated with hormone replacement therapies. The invention is based, in part, on the remarkable efficacy and safety of triphenylethylene derivatives in treating atrophic vaginitis in women.

The terms used in this specification generally have their ordinary meanings in the art, within the context of this invention and in the specific context where each term is used. Certain terms are defined below to provide additional guidance in describing the compositions and methods of the invention and how to make use of them.

Definitions

The term "estrogen receptor" refers to any protein in the nuclear receptor gene family that binds to estrogen. Human estrogen receptor in the present invention includes the alpha-receptor isoform (referred to herein as "ER-alpha") in addition to any additional isoforms as recognized by those of skill in the biochemistry arts.

The term "selective estrogen receptor modulator" (or "SERM") is a compound that exhibits activity as an agonist or antagonist of an estrogen receptor (e.g., ER-alpha) in a tissue dependent manner. Thus, as will be apparent to those of skill in the biochemistry arts, compounds of the invention that function as SERMs can act as estrogen receptor agonists in some tissues (e.g., bone, vagina, bladder and urethra) and as antagonists in other tissues types such as breast.

The terms "estrogenic effect" refer to the efficacy of a compound that exhibits agonistic activity of an estrogen receptor in a tissue dependent manner. Efficacy is measured by the induction of keratinization of the vaginal epithelium. Thus, as apparent by those of skill in the field of cytology, the induction of vaginal cornification best reflects the estrogenic effect of a pharmaceutical compound.

The terms "thrombogenic events" as used herein refers to the formation or presence of a thrombus; clotting within a blood vessels, which may cause infarction of tissues supplied by the vessel resulting from a pharmaceutical compound.

The terms "climacteric symptom" as used herein refers to the symptom of the climacteric which is the episodic disturbance consisting of sudden flushing and perspiration referred to as a hot flush or flash.

The terms "anti-proliferative effect" as used herein refers to the inhibition of estrogenic actions in the uterus by reducing the proliferative actions of estrogen, and allowing uterine cell differentiation to occur. The anti-proliferative effect of progesterone inhibits the effects of estrogen stimulation on the endometrium through the process of cell differentiation. The anti-proliferative effect on the uterus occurs because it is the mitotic activity that has to be inhibited to prevent the occurrence of endometrial hyperplasia.

The terms "adverse uterine effects" refers to the stimulatory effects of estrogen on the endometrium. It is the adverse effect of when the endometrium is under continuous estrogen stimulation that it undergoes proliferation, hyperplasia and then may progress to a histological uterine malignancy.

The term "subject" as used herein refers to a female patient in need of treatment of symptoms associated with atrophic vaginitis. "Patient", as used herein, may refer to a human or animal patient. In certain embodiments, where the method of treatment is carried out with a triphenylethylene derivative compound, the subject is a hysterectomized patient. In other embodiments, where the method of treatment involves a combination therapy, the subject is a non-hysterectomized patient.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless specified otherwise, all values provided herein can be assumed to include the term about.

The phrase "pharmaceutically acceptable" refers to molecular entities and compositions that are "generally regarded as safe" (GRAS), e.g., that are physiologically tolerable and do not typically produce an allergic or similar untoward reaction, such as gastric upset, dizziness and the like, when administered to an animal. Preferably, as used herein, the term "pharmaceutically acceptable" means approved by a regulatory agency of the Federal or state government or listed in the U.S. Pharmacopeia or other generally recognized pharmacopeia for the use in animals.

The term "carrier" refers to a diluent, adjuvant, excipient, or vehicle with which the compound is administered. Such pharmaceutical carriers can be sterile liquids, due to its high in solubility in water, oils, including those of petroleum, animal, vegetable or synthetic origin, such as peanut oil, soybean oil, mineral oil, sesame oil and the like. Carriers such as micelles or dextran can be used to deliver the agent in an aqueous solution or suspension. E. W. Martin describes suitable pharmaceutical carriers in "Remington's Pharmaceutical Sciences".

The term "amount" as used herein refers to quantity or to concentration as appropriate to the context. In the present invention, the effective amount of a triphenylethylene derivative compound refers to an amount sufficient to treat symptoms associated with atrophic vaginitis. The effective amount of a drug that constitutes a therapeutically effective amount varies according to factors such as the potency of a particular drug, the route of administration of the formulation, and to the mechanical system used to administer the formulation. A therapeutically effective amount of a particular drug can be selected by those of ordinary skill in the art with due consideration of such factors.

Pharmaceutical Formulation

SERM

Selective estrogen receptor modulators (SERMs) and/or its analog, derivative, isomer, metabolite, pharmaceutically acceptable salt, pharmaceutical product, hydrate, N-oxide, or any combination thereof may be used in the compositions and methods of this invention. The term selective estrogen receptor modulator includes both estrogen agonist and estrogen antagonists and refers to compounds that bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues.

SERM-like activity can be classified within four groups by chemical structure: triphenylethylene compounds, benzopyrans, naphthalenes, and benzothiophenes. SERMs encompassed by the present invention include, but are not limited to the following triphenylalkylenes such as triphenylethylenes, which include tamoxifen and associated compounds which are disclosed in U.S. Pat. No. 4,536,516, the disclosure of which is hereby incorporated by reference; 4-hydroxy tamoxifen which is disclosed in U.S. Pat. No. 4,623,660, the disclosure of which is hereby incorporated by reference; toremifine, droloxifene, yoremifene, idoxifene (Pyrrolidine, 1-1-[4-[–1-(4-iodophenyl)-2-phenyl-1-Butenyl]phenoxy]ethyl]) and associated compounds which are disclosed in U.S. Pat. No. 4,839,155, the disclosure of which is hereby incorporated by reference; clomiphene, enclomiphene and zuclomiphene; benzothiphene derivatives such as raloxifene (methanone, [6-hydroxy-2-(4-hydroxyphenyl) benzo[b]thien-3-yl][4-[2-(1-piperidinyl)ethoxy] phenyl]-, hydrochloride) and associated compounds which are disclosed in U.S. Pat. No. 4,418,068, the disclosure of which is hereby incorporated by reference; and LY 353381; benzopyran derivatives such as EM 800 (SCH 57050) and its metabolite EM 652; naphthalene derivatives such as lasofoxifene (CP 336,156); chromans such as levormeloxifene or their analogs, derivatives, isomers, or metabolites thereof, or their pharmaceutically acceptable salts, esters, N-oxides, or mixtures thereof. Preferably, the triphenylethylene compounds are used in the present invention.

Triphenylethylene Compounds

A "triphenylethylene" or "triphenylethylene compound" as used herein is defined in the $2^{nd}$ edition of Estrogen And Progestogens in Clinical Practice, Churchill, Livingstone hereby incorporated by reference (Silfen et al., S. L., Climacteric 1999; 2: 268-283). Included in this definition are non-steroidal estrogens described in the aforementioned reference. Other triphenylethylene compounds included in this definition are triphenylethylene derivatives, triphenylethylene metabolites and triphenylethylene precursors. Also included are the mixtures of more than one triphenylethylene or triphenylethylene compound.

Triphenylethylenes compounds include, but are not limited to tamoxifen, 4-hydroxy tamoxifen, toremifine, droloxifene, yoremifene, idoxifene, clomiphene, enclomiphene and zuclomiphene, and associated compounds. In a specific embodiment, the triphenylethylene compound is tamoxifen.

Tamoxifen is a selective estrogen receptor modulator. The chemical name is 1-(p-dimethylamino-ethoxphenyl)-2-ethyl-1, 2-diphenylethylene. Tamoxifen has an empirical formula of $C_{26}H_{29}NO$, and has a molecular weight of 371.521. In the present invention, both the cis and trans isomers is contemplated.

In the present invention, the preferred form is the active form of tamoxifen, tamoxifen citrate. The chemical name of tamoxifen citrate is (Z) 2-[4-(1,2-diphenyl-1-butenyl) phenoxy]-N, N-dimethylethanamine 2-hydroxy-1,2,3-propanetricarboxylate. Tamoxifen citrate has an empirical formula of $C_{26}H_{29}NO.C_6H_8O_7$ and has a molecular weight of 563.62. The structure is:

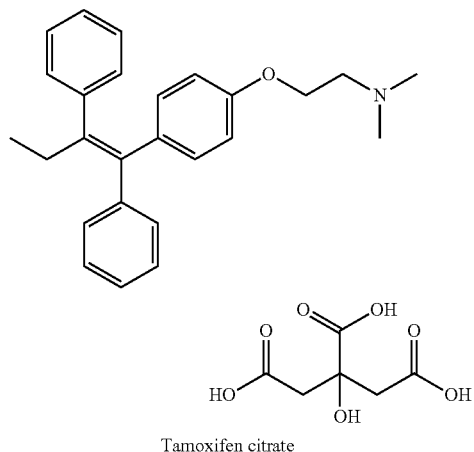

Tamoxifen citrate

The amount of tamoxifen citrate present in the composition depends on the strength of the final composition. In one embodiment, tamoxifen citrate is present in amounts ranging from about 0.2 mg per dose to about 200 mg per dose, preferably from about 1 mg to about 30 mg per dose, preferably from about 2 mg to about 20 mg per dose, more preferably from about 10 mg to about 20 mg per dose. In particular suppository dosage forms, the tamoxifen citrate is present in amounts from about 1 mg to about 30 mg per dose, preferably from about 10 mg to about 20 mg per dose. In particular cream dosage forms, tamoxifen citrate is present in amounts from about 1 mg to about 30 mg per dose, preferably from about 10 mg to about 20 mg per dose.

Progesterone

Progesterone is a naturally occurring steroidal sex hormone and is defined as compound, which acts on the uterus to induce endometrial changes characteristic of pregnancy and which maintain pregnancy in animals. The progesterone receptor is under the dual control of estrogen and progesterone, which act sequentially to regulate cellular concentrations of progesterone receptor. The endometrial progesterone receptor is increased by estrogen via an estrogen-mediated increase in progesterone receptor messenger RNA levels and increased protein synthesis. It is down regulated by its own ligand, progestogen, at the transcriptional and posttranscriptional levels. In the human uterus, high concentrations of progesterone result in an inhibition of estrogen actions. The reduction in estrogen receptor synthesis is due to progestogen-mediated decrease in levels of estrogen receptor messenger RNA. Overall, by reducing the proliferative actions of estrogen, progesterone allows for differentiation to occur. It is thus the biochemical machinery, induced by estrogen, and the mitotic activity that have to be inhibited to prevent endometrial hyperplasia.

Progesterone has a chemical formula pregn-4-ene-3, 20-dione. It has a molecular weight of 314.47 and an empirical formula $C_{21}H_{30}O_2$. The structural formula is:

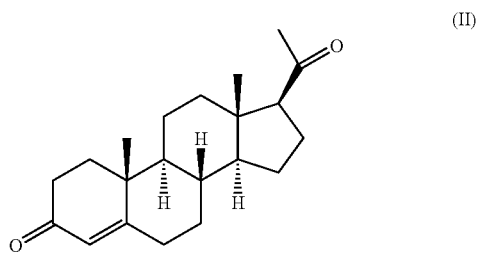

Overall, the aim of hormone therapy when using progesterone is to prevent or limit endometrial hyperplasia associated with estrogen use. A dosage of 100 mg micronized progesterone given orally is sufficient to inhibit endometrial estrogen receptor levels and mitotic activity (King et al., *Fertil Steril* 1986; 46: 1062-1066). A dosage of 100 mg micronized progesterone given vaginally more often induced (p<0.005 at six months and p<0.001 after 1 year) a functional like secretory endometrium causing a cyclic monthly cycle resulting in shedding of the endometrium (Ferrero et al., *Minerva Ginecol* 2002; 54: 519-30). The relative potency of an oral dose of 200 mg micronized progesterone is equivalent to that of a topical dose of 80 mg micronized progesterone (Herman et al., Bioequivalence of over-the counter (OTC) progesterone cream (PC). Presented at the Amer Soc Clin Pharm annual meeting, Mar. 25, 2004, Miami Beach Fla.). Given that an oral dose of 100 mg of micronized progesterone provides sufficient endometrial protection, an approximate dose of topical 40 mg micronized progesterone should provide sufficient endometrial protection. In addition, evidence shows that a dose of transdermal 30 mg progesterone has an antiproliferative effect on estrogen-stimulated postmenopausal endometrium through endometrial biopsy (Leonetti et al., *Fertil Steril* 2003; 79:221-22). Further, the serum concentration of 25 mg and 50 mg progesterone administered as vaginal suppositories, were similar between both groups (7.27 ng/ml and 8.84 ng/ml respectively) (Von Eye Corleta et al., *Gynecol Obstet Invest* 2004; 58 (2): 105-8).

A vaginal route for progesterone was chosen because progesterone is taken up preferentially by the endometrium. When comparing serum and endometrial concentrations of progesterone when the progesterone is given intramuscularly compared to intravaginally, serum progesterone levels in the vaginal group were lower than the intramuscular group yet, the endometrial tissue concentration of vaginal progesterone was higher (Ficicioglu et al., *Gynecol Endocrinol* 2004; 18: 240-243). Evidence using labeled material (99m Tc-pertechnetate) indicates a preferential vagina to uterus distribution of materials introduced into the vagina (Cicinelli et al., *Fertil Steril* 2001; 76: 1108-12). Overall, progesterone used vaginally has a high local effect on the endometrium, while reducing systemic side effects due to the lower serum concentrations thus making it an ideal route of administration.

Further, there are studies that show micronized progesterone (progesterone) is safer than synthetic progesterone (progestin) such as Medroxyprogesterone Acetate (MPA). Table 1 compares Medroxyprogesterone (MPA) versus Micronized Progesterone (MP), demonstrating the relative safety of MP over MPA (The writing Group for the PEPI Trial; Effects of Estrogen or Estrogen/Progestin Regimens on Heart Disease-Risk Factors in Postmenopausal Women; *JAMA*, January 1995; 273:3; 199-208); Physicians Desk Reference, 44th edition, 1990; Bolaji, *EUROBS*, 48 (1993) 61-68; Darj, E., *Gynecol. Endocrinol.* 1993; 7:111-114; Rylance P B, Br Med J (Clin Res Ed) 1985 Jan. 5; 290 (6461) 13-4; Sammour M B, *Acta Obstet Gynec Scand.* 1975; 54: 195-202; Sammour M B, Clin Exp Hyper-Hyper in Preg. 1982; B1: 455-78; Minshall et al., *Journal of Clinical Endocrinology and Metabolism* 1998: 83(2): 649-59; Minshall et al., *FASEB J* 1998; 1998: 12(13) p. 1419-1429. Rosano et al., *J Am Coll Cardiol* 2000; 36(7): 2154-9; Estrogen and Progestogens in Clinical Practice; Harcourt Brace & Co, 1998 ISBN 0443047065; Montplaisir J., *Menopause* 2001; 8: 10-16; Arafat E S, *Am J Obstet Gynecol* 1998; 159: 1203-09; Fitzpatrick L A, *Journal of Women's Health&Gender-Based Medicine* 2000; 9: 381-387).

TABLE 1

| | |
|---|---|
| Lipid Profile | MPA: adversely effects lipid profile and negates the beneficial effects of estrogen.<br>MP: does not negate the beneficial effects of estrogen and modestly improves cholesterol levels. |
| Liver function | MPA: contraindicated in patients with liver dysfunction.<br>MP: does not effect liver enzymes or cause liver related side effects. |
| Cardiovascular Events | MPA: may cause fluid retention and edema, increases incidence of CHD, stroke and VTE, and diminishes the cardio-protective effects of estrogens.<br>MP: has antihypertensive action and can be safely used to treat preeclampsia. And with estrogen, prevents coronary vasospasms (in rhesus monkeys) and enhances the beneficial effects of estrogen on exercised-induced myocardial ischemia in menopausal women. |
| Glucose/ Insulin | MPA: has been found to cause deterioration of glucose tolerance or hyperinsulemia or both.<br>MP: augments the pancreatic response to glucose and increases the release of insulin. |
| Sleep and Mood | MPA: can cause insomnia, mental depression, and anxiety.<br>MP: improves the quality of sleep and has sedative properties. |
| Quality of life/ menopausal symptoms | When compared with MPA-containing regimen, women using MP-containing HRT experienced significant improvement in symptoms in 80%. |

In addition, micronized progesterone is a better choice because the results of the American WHI study caused considerable concern among hormone replacement users with the use of Medroxyprogesterone. The placebo-controlled trial of an oral continuous combined conjugated equine estrogens (CEE) plus Medroxyprogesterone acetate (MPA) regimen was prematurely discontinued because it showed an increase breast cancer risk in the CEE plus MPA arm (Writing Group for the Women's Health Initiative. Risks and Benefits of Estrogen Plus Progestin in Healthy Postmenopausal Women. Principal results from the Women's Health Initiative Randomized Control Trial. JAMA 2002; 288: 321-33). A different study evaluated the impact of the type of progestogen used and the results demonstrated that the risk of breast cancer increased significantly for users of estrogens combined with progestogens (R 1.3, 95% CI 1.1-1.5), but this increase risk was limited to synthetic progestins (RR 1.4, 95% CI 1.2-1.7); there was no evidence of increased risk associated with the use of estrogens combined with micronized progesterone (RR 0.9, 95% CI 0.7-1.2) (Fournier et al., *Int J Cancer* 2005; 114: 448-454). There was no evidence of increasing risk with increasing duration of HRT exposure, except for the oral estrogens combined with synthetic progestins. It is evident that the association between HRT use and breast cancer risk most likely varies according to the type of progestogen used.

In the present invention, micronized progesterone is the preferred progesterone compound. The amount of progesterone present in the composition may depend on the strength of the final composition. In one embodiment, the progesterone compound is present in amounts ranging from about 5 mg to about 500 mg per dose, preferably the range is from about 5 mg to about 100 mg per dose, more preferably from about 15 mg to about 50 mg per dose, which is sufficient to oppose the uterine proliferative activity of the triphenylethylene derivative compound. In a different embodiment, the progesterone compound is present in amounts ranging from about 7.5 mg to about 30 mg per dose. In yet other embodiments of the invention, the progesterone compound is present in amounts from about 15 mg to about 75 mg per dose.

Additional Constituents

The triphenylethylene compounds and progesterone of the present invention are formulated into a pharmaceutical composition with additional constituents for vaginal administration by way of suppositories, creams, foams, gels (including, but not limiting to aqueous solutions and suspensions), ointments, tablets, ovules, pessaries and rings, and other known pharmaceutically acceptable carriers known in the art.

In one embodiment of the invention, the triphenylethylene is formulated with a fatty base. The base may be selected from, but is not limited to JAB base, JC base, polyethylene glycol base, emollient cream, vanishing cream light, vanpen base, cosmetic HRT base, or mixtures thereof. When the mode of administration is through a vaginal suppository, preferably, the base is JAB. JAB base is a combined formulation containing Base K, Base C and Base M. Base K is composed of PEG-8 distearate. Base C is composed of a hydrogenated vitamin oil. Base M is composed of Vitamin E Acetate. The range for the JAB base in a suppository is from about 0.1 gm to about 1.4 gm, preferably about 1.25 gm. The total weight of the active and inactive ingredients is about 5 gm or less, preferably 4 gm or less, more preferably 1000 mg or less, or 300 mg or less.

In another embodiment of the invention, the triphenylethylene derivative and progesterone are formulated together in a fatty base. The base may be selected from, but is not limited to JAB base, JC base, polyethylene glycol base, emollient cream, vanishing cream light, vanpen base, cosmetic HRT base, or mixtures thereof. When the mode of administration is through a vaginal suppository, preferably, the base is JAB. JAB base is a combined formulation containing Base K, Base C and Base M. Base K is composed of PEG-8 distearate. Base C is composed of a hydrogenated vitamin oil. Base M is composed of Vitamin E Acetate. The range for the JAB base in a suppository is from about 0.1 gm to about 1.4 gm, preferably from about 1 gm to about 1.3 mg, more preferably about 1.2 gm, more preferably about 1.1 gm. The total weight of the active and inactive ingredients is about 5 gm or less, preferably 4 gm or less, more preferably 1000 mg or less or 300 mg or less.

When the compound is formulated into a vaginal cream, the preferred base is JC base. The JC base is composed of emollient cream and Base M. The range for the JC base in a cream is from about 0.5 gm to about 2.0 gm, preferably from about 0.8 gm to about 1.3 gm, more preferably about 0.9 gm.

The amount and concentrations of the constituents will correlate to an appropriate dosage form. For example, the suppository size will depend on the concentration and amount of ingredients. Preset suppository molds are contemplated in the present invention. The mold sizes range from approximately 0.5 gm to about 5.0 gm, preferably 1.28 gm, 1.4 gm, or 1.9 gm mold sizes. Cream dosages/volumes will depend on the applicator being used. The range for cream dosages may vary from about 0.5 gm to about 4.0 gm, preferably from about 0.5 gm to about 2.0 gm.

The pharmaceutical composition may include one or more additives, depending on the pharmaceutically acceptable carrier, a preservative, a dye, a binder, a suspending agent, a dispersing agent, a colorant, a disintegrate, an excipient, a diluent, a lubricant, a plasticizer, an oil or any combination of any of the foregoing. In particular embodiments, silica gel is used as a suspending agent. The amount of suspending agents will depend on the dosage and size of application, varying from about 0.01 g to about 1 gm, preferably from about 0.01 g to about 0.1 gm, preferably from about 0.01 gm to about 0.05 gm, more preferably from about 0.01 gm to about 0.03 gm. However, one skilled in the art will be able to best determine the amount of such additives. Examples of additional additives include, but are not limited to, sorbitol; talc; stearic acid; and dicalcium phosphate.

Suitable pharmaceutically acceptable additives include, but are not limited to, ethanol; water; glycerol; aloe vera gel; allantoin; glycerin; vitamin A and E oils; mineral oil; PPG2 myristyl propionate; vegetable oils and solketal.

Suitable binders include, but are not limited to starch; gelatin; natural sugars, such as glucose, sucrose and lactose; corn sweeteners; natural and synthetic gums, such as acacia, tragacanth, vegetable gum, and sodium alginate; carboxymethylcellulose; polyethylene glycol; waxes; and the like.

Suitable lubricants include, but are not limited to, sodium oleate, sodium stearate, magnesium stearate, sodium acetate, and the like.

The composition may also include suitable preservatives, e.g., sodium benzoate, and other additives that may render the composition more suitable for application, e.g., sodium chloride, which affects the osmolarity of the preparation.

Suitable dispersing and suspending agents include, but are not limited to synthetic and natural gums, such as bentoite, vegetable gum, tragacanth, acacia, alginate, dextran, sodium carboxymethylcellulose, methylcellulose, polyvinyl-pyrrolidone and gelatin.

A suitable pharmaceutical diluent is, but is not limited to, water.

Additionally, various agents may be used to change the pH of the composition as necessary, including, for example, hydrochloric acid or sodium hydroxide, and antioxidants such as citric acid, ascorbic acid, fumaric acid and malic acid. Other possible antioxidants include palmitate, butylated hydroxyanisole, propylgallate, sodium ascorbate, and sodium metabisulfite. In particular embodiments, citric acid (0.1%) is used.

Modes of Administration

Many methods may be used for vaginal administration of the formulation of the invention. These include vaginal administration of creams, suppositories, foams, gels (including, but not limited to aqueous solutions and suspensions) ointments, tablets, ovules, pessaries and rings.

In certain embodiment of the invention, the triphenylethylene derivatives may be formulated together or separately. The effective dose may vary, depending upon factors such as the condition of the patient, the severity of the symptoms of the disease and the manner in which the pharmaceutical composition is administered. The composition is formulated, preferably per unit dose, or labeled for dispensing an amount, such that each dosage contains from about 0.2 mg to about 200 mg per unit dose of tamoxifen.

In a certain embodiment of the invention, the triphenylethylene derivative and progesterone compounds may be formulated together or separately. The effective dose may vary, depending upon factors such as the condition of the patient, the severity of the symptoms of the disease and the manner in which the pharmaceutical composition is administered. The compositions are formulated, preferably as per unit dose, or labeled for dispensing an amount, such that each dosage contains from about 0.2 mg to about 200 mg per unit dose of triphenylethylene derivative, and from about 5 mg to about 500 mg progesterone per unit dose.

The pharmaceutical composition may be in a "unit dosage form", which refers to physically discrete units suitable as unitary dosages for human subjects and other mammals, each unit containing a predetermined quantity of active material calculated to produce the desired therapeutic effect, in association with one or more of the above-described suitable pharmaceutical diluents, excipients or carriers.

Methods of Treatment

The pharmaceutical composition of the present invention may be administered to a subject, preferably a human being, in need thereof to treat symptoms associated with atrophic vaginitis. In one embodiment, for treatment of symptoms of atrophic vaginitis with a triphenylethylene derivative compound, the subjects are hysterectomized patients. In an alternative embodiment, for treatment with a combination therapy of a triphenylethylene derivative compound and a progesterone compound, the subjects are non-hysterectomized patients.

The invention describes both a safe and clinically effective formulation necessary to treat vaginal symptoms resulting from surgical menopause, iatrogenic menopause, natural menopause and conditions leading to suppressing estrogen levels manifesting as menopause (See Table 2).

TABLE 2

1. Anorexia Nervosa
2. Chromophobe Adenoma
3. Functional Hypothalamic Amenorrhea
4. Gonadal Failure
5. Gonadal Streaks
6. Gonadotrophin-Resistant Ovary Syndrome
7. Hypogonadotrophic Hypogonadism
8. Hypothalamic Dysfunction
9. Hypothalamic Failure TABLE 2-continued 10. Isolated Gonadotrophin Deficiency
11. Pituitary Destruction
12. Polycystic Ovary Syndrome
13. Ovarian Destruction
14. Premature Ovarian Failure
15. Pure Gonadal Dysgenesis
16. Pituitary Failure
17. Hypothalamic etiology
18. Ovarian etiology
19. Pituitary etiology
20. Pituitary Dysfunction The pharmaceutical composition may be used to treat various conditions and symptoms of the vagina, urethra and bladder including but not limited to pain, burning, irritation itching, dryness, pressure, urinary frequency and incontinence. The compound, pharmaceutical composition, or unit dosage form of the present invention may be administered alone at appropriate dosages defined by routine testing in order to obtain greatest efficacy minimizing any potential side effects.

The daily dosage of the compound of the present invention may vary according to a variety of factors such as underlying disease states, the individual's condition, weight, age and the mode of administration. For vaginal administration, in certain embodiments, where both Tamoxifen and progesterone are administered as a single dosage form or as co-administered, combined therapies include, as nonlimiting examples, 20 mg Tamoxifen:15 mg progesterone, 10 mg Tamoxifen:7.5 mg progesterone, and 30 mg Tamoxifen:30 mg progesterone.

In other embodiments, the pharmaceutical composition can be provided in unit dosage forms containing most preferably from about 20 mg per dose of Tamoxifen citrate, preferably to about 10 mg per dose, more preferably to about 5 mg per dose of the present invention for the symptomatic adjustment of the dosage to the patient to be treated. Further, pharmaceutical compositions can be provided in unit dosage forms containing Tamoxifen citrate and progesterone most preferably from about 20 mg:30 mg per unit dose respectively, preferably to about 10 mg:15 mg per unit dose, more preferably to about 5 mg:7.5 mg per unit dose of the present invention for the symptomatic adjustment of the dosage to the patient to be treated. In particular embodiments, the composition is administered once a week. In other embodiments, the composition is administered twice or three times a week.

Vaginal administration may continue for at least 3 months, preferably at least 6 months, more preferably at least 12 months. In a specific embodiment, treatment will continue at least 18 months, more preferably at least 24 months and most preferably at least 60 months.

In one embodiment of the invention, the dosing schedule is one nighttime application each day for at least one week, preferably at least two weeks, followed by at least one application each week, preferably at least two applications each week, for at least one year.

The present invention will be better understood by reference to the following proposed compound formulation examples, which is provided as exemplary of the invention, and not by way of limitation.

EXAMPLES

Example 1

Formulation of Triphenylethylene Derivative in Suppository Form

The present example provides a formulation of a pharmaceutical composition to treat symptoms associated with atrophic vaginitis. Table 3 summarizes the components and respective amounts of each component.

TABLE 3

| | |
|---|---|
| Tamoxifen Citrate | 0.0200 gm |
| Silica Gel | 0.0150 gm |
| Base JAB: (fatty base) | 1.2485 gm |
| Suppository Volume | 1.2835 gm |
| Citric Acid 0.1% at 0.0013 gm | For pH Adjustment |

Example 2

Formulation of Triphenylethylene Derivative in Cream Form

The present example provides a formulation of a pharmaceutical composition to treat symptoms associated with atrophic vaginitis. Table 4 summarizes the components and respective amounts of each component.

TABLE 4

| | |
|---|---|
| Tamoxifen Citrate USP | 0.0200 gm |
| Propylene Glycol USP | 0.0333 ml |
| JC Base | 0.9467 gm |
| (Base B and Base M) | |
| Base B is emollient cream | |
| Base M is Vitamin E Acetate | |
| USP Liquid (1 IU/mg) | |
| Total volume/per dose | 1.000 gm |

Example 3

Formulation of Triphenylethylene Derivative and Progesterone in Suppository Form The present example provides a formulation of a pharmaceutical composition to treat symptoms associated with atrophic vaginitis. Table 5 summarizes the components and respective amounts of each component.

TABLE 5

| | |
|---|---|
| Tamoxifen Citrate | 0.0200 gm |
| Progesterone | 0.0300 gm |
| Silica Gel | 0.0150 gm |
| Base JAB: (fatty base) | 1.2215 gm |
| Suppository Volume | 1.2865 gm |
| Citric Acid 0.1% at 0.0013 gm | For pH Adjustment |

Example 4

Formulation of Triphenylethylene Derivative and Progesterone in Cream Form

The present example provides a formulation of a pharmaceutical composition to treat symptoms associated with atrophic vaginitis. Table 6 summarizes the components and respective amounts of each component.

TABLE 6

| | |
|---|---|
| Tamoxifen Citrate USP | 0.0200 gm |
| Progesterone | 0.0300 gm |
| Propylene Glycol USP | 0.0333 ml |
| JC Base | 0.9167 gm |
| (Base B and Base M) | |
| Base B is emollient cream | |
| Base M is Vitamin E Acetate | |
| USP Liquid (1 IU/mg) | |
| Total volume/per dose | 1.000 gm |

Example 5

A Pilot Study to Examine the Efficacy and Safety of a Tamoxifen Vaginal Suppository in Postmenopausal Hysterectomized Patients with Atrophic Vaginitis The present Example details a pilot study to investigate effectiveness and safety of a tamoxifen vaginal suppository in the treatment of atrophic vaginitis in postmenopausal hysterectomized patients.

For this pilot study, the following specific aims are proposed:

Primary Aim: To estimate the efficacy in treating atrophic vaginitis as determined by an improvement in the Vaginal Maturation Index, an improvement in Menopausal Quality of Life, improvement in patient self-assessment of vaginal dryness, and in normalization of vaginal pH.

Secondary Aim: To estimate the safety in treating atrophic vaginitis as determined by Tamoxifen serum concentrations.

Research Design and Methods

Human Subjects

There are 20 subjects enrolled in the study. This study has been designed to follow FDA guidance and is limited in the inclusion/exclusion criterion to also follow FDA guidance.

Inclusion Criteria:
1. The study population includes women of all races without uterus.
2. Participants with ages of 45 years and older are recruited.
3. Women have follicle-stimulating hormone (FSH) levels of greater than or equal to 40 mIU/ml.
4. The presence of vaginal dryness on study visit 1.
5. A Vaginal Maturation Index of less than 50 on study visit 1.
6. A vaginal pH greater than 5 on study visit 1
7. A normal mammogram within one year prior to study visit 1, per subject self report.
8. The patient is able to use the vaginal suppository.
9. The patient is able to understand and sign an informed consent.

Exclusion Criteria
1. Use of the following drugs or agents: coumadin or heparin, any estrogen within 3 months of enrollment, use of over-the-counter phytoestrogens within 3 months of enrollment.
2. A medical history of a thromboembolic event or pulmonary embolus.
3. A blood pressure reading greater than 180 systolic or 105 diastolic at study visit 1.
4. History of breast cancer or a mammogram that is positive or suspect for breast cancer or breast cancer occurring in an identical twin prior to enrollment.
5. Known or suspected estrogen-dependant neoplasia.
6. Myocardial infarction within 6 months of enrollment.
7. Coronary heart disease requiring antiarrhythmics or digitalis.
8. Congestive heart failure.
9. Stroke or TIA.
10. A known hypersensitivity to the ingredients.
11. Malignant melanoma.
12. Any cancer (except nonmelanonomatous skin cancer) diagnosed less than 5 years prior to enrollment.
13. Chronic liver disease.
14. Any other major life-threatening illness.

Dosage and Administration

Participants are given the following treatment: vaginal suppository containing 20 mg Tamoxifen per day for two weeks and then three times per week thereafter (n=20). Participants are instructed to refrigerate the test drug. They are told how to insert the test drug (using the applicator, place the study drug deep into the vagina) and the dosing schedule: every day for two weeks and then begin a maintenance regimen using the study drug on Mondays, Wednesdays and Fridays.

Study Visit 1

The first visit includes the following:

Each participant reads the consent form and has her questions answered, then signs and dates the form.

The participant is then asked to fill out a questionnaire relating to her past medical history. This is similar to a routine history and physical examination questionnaire.

The participant undergoes an assessment of menopausal quality of life, using the MenQOL questionnaire. This is a validated questionnaire commonly used in menopause research. Either the principal investigator or the CRC nurse ensures that the questionnaire is completely filled out.

The severity of vaginal atrophy symptom vaginal dryness is graded by the patients using a rating scale (range: 'none' to 'extreme' for the symptom). The study measures a mean patient rating of vaginal dryness on a rating scale where "0" means "no" dryness and "10" means "extreme" dryness. The study uses a rating scale that has been used to assess symptomatic vaginal dryness in menopausal patients on hormone therapy in several studies. Participants are given a vaginal dryness diary card on this visit, to be returned at Visit 2. The participant is then instructed to fill it out on the day prior to Visit 2.

The participant undergoes a gynecological examination by the principal investigator, similar to a routine gynecological exam. Blood pressure is also checked. During the exam, a vaginal cytology for Vaginal maturation index and a vaginal pH is obtained. A validated scoring system for quantifying estrogen-deficient urogenital atrophy is measured through a Vaginal Maturation Index (VMI). The VMI is measured as=(% Intermediate Cells×0.5)+% Superficial Cells. In this study, vaginal atrophy is defined as a vaginal maturation index of less than 50 at inclusion. VMI is an indicator of the estrogenic effect on the vaginal epithelium, with a range of 0-49 indicating an absent or low estrogenic effect, 50-64 moderate estrogenic effect, and 65-100 high estrogenic effect. Vaginal cytology specimens are collected. Specimens are obtained by scraping the right and left lateral vaginal walls (midway between the fornix and introitus) with a plastic spatula. The cells and mucous samples that are collected are mixed in a fixative to form a cell suspension. The number of superficial and intermediate cells are counted and the percentage of each cell type calculated. These percentages are utilized in the above noted equation to determine the VMI.

Vaginal pH is then checked. A vaginal pH test is done at baseline and again at months 3 and 6. To permit a vaginal pH reading to be obtained easily, safely, and reliably from the lateral outer third of the vagina, a specific device is chosen, pHEM-ALERT®, developed by FemTek LLC. The pHEM-ALERT® test provides a method to measure vaginal pH. It is comprised of a disposable plastic probe with pH paper on one end, a color chart and a package insert. The plastic probe is inserted into the vagina and after 5 seconds of vaginal contact, the color of the paper is compared with a colorimetric scale on an enclosed card, and the pH value is determined.

A venous blood sample (approximately 10 ml or 2 teaspoon) is taken to measure serum Tamoxifen and Follicle Stimulating Hormone.

To be eligible to continue to study visit 2, subjects must have an FSH>40, a vaginal pH>5 and a VMI score <50. All of these results are consistent with atrophic vaginitis resulting from menopause. Once it is confirmed that the subject has met these eligibility criteria, she is scheduled for Study 2. If eligibility criteria are not confirmed, the subject is informed that her study participation has ended.

Study Visit 2

If the participant meets eligibility for the study based upon the first visit, the subject returns for study visit 2. The participant hands in the vaginal dryness Diary Card given at Study Visit 1 on this visit and it is reviewed. The subject is given a three-month supply of vaginal dryness Diary Cards and is instructed to complete one diary card per month, on the last day of each month of study drug. The subject is also instructed to refrain from sexual intercourse for 24 hours prior to Study Visit 3.

Study Visit 3

Study visit 3 takes place in the last two weeks of month three. The participant completes the MenQOL questionnaire. The three one-month diary cards are collected and reviewed on this visit. Blood pressure is also checked. A pelvic exam is performed, which includes checking the vaginal pH and taking a vaginal cytology. This visit is timed to occur roughly five hours after placement of the suppository. A venous blood sample (approximately 10 ml or 2 teaspoons) is also taken to measure a serum tamoxifen.

The collection of all data is summarized in the following table.

TABLE 7

| Data Collection Schedule (0-3 months) | | |
|---|---|---|
| Variable Assessed | Baseline | Month 3 |
| History and physical | X | |
| Vaginal pH | X | X |
| Vaginal cytology | X | X |
| Self-assessment of vaginal dryness | X | X |
| Serum Tamoxifen | X | X |
| Serum Follicle Stimulating Hormone | X | |
| MenQOL questionnaire | X | X |

Biostatistical Design and Analysis

Sample Size. This study enrolls a convenience sample of 20 participants. This sample size yields 95% confidence intervals that is ±44% of the standard deviation of the point estimates.

The primary endpoints are changes in the Vaginal Maturation Index, Menopausal Quality of Life, self-assessment of vaginal dryness and vaginal pH defined as the difference between the baseline and the 3-month follow-up measurements. The secondary endpoint are the changes in serum Tamoxifen concentrations defined as the difference between the baseline and the 3-month follow-up measurements. Descriptive statistics for the continuous study endpoints include mean, median, standard deviation, and 95% confidence intervals. Descriptive statistics provided for categorical endpoints include frequencies, percents, and 95% confidence intervals. Missing values of a variable are to be imputed using the last observed value for the participant. Descriptive statistics are provided with and without imputation of missing values.

Example 6

Formulation of Triphenylethylene Derivative with and without Progesterone in Suppository and Cream Form The present example provides formulations for pharmaceutical compositions to treat symptoms associated with atrophic vaginitis. Tables 8 and 9 summarize the components and respective amounts of each component.

TABLE 8

| Suppository Formulations | | | | |
|---|---|---|---|---|
| | 20 mg | 10 mg | 20 mg Tamoxifen/15 mg Progesterone Suppository | 10 mg Tamoxifen/7.5 mg Progesterone Suppository |
| Tamoxifen Citrate USP | 0.0200 gm | 0.0100 gm | 0.0200 gm | 0.0100 gm |
| Progesterone USP, PCCA Special Micronized | | | 0.0150 gm | 0.0075 gm |
| Vitamin E Acetate USP Liquid | 0.1000 gm | 0.1000 gm | 0.1000 gm | 0.1000 gm |
| Silica Gel Micronized | 0.0150 gm | 0.0150 gm | 0.0150 gm | 0.0150 gm |

TABLE 8-continued

Suppository Formulations

|  | 20 mg | 10 mg | 20 mg Tamoxifen/15 mg Progesterone Suppository | 10 mg Tamoxifen/7.5 mg Progesterone Suppository |
|---|---|---|---|---|
| JAB Base (Fatty Base) | 1.1485 gm | 1.1575 gm | 1.1350 gm | 1.1508 gm |

TABLE 9

Cream Formulations

|  | 20 mg/gm Cream | 10 mg/gm Cream | 20/15 mg/gm Cream | 10/7.5 mg/gm Cream |
|---|---|---|---|---|
| Tamoxifen Citrate USP | 0.0200 gm | 0.0100 gm | 0.0200 gm | 0.0100 gm |
| Progesterone USP, PCCA Special Micronized |  |  | 0.0150 gm | 0.0075 gm |
| Vitamin E Acetate USP Liquid | 0.1000 gm | 0.1000 gm | 0.1000 gm | 0.1000 gm |
| Propylene Glycol, USP | 0.0333 ml | 0.0333 ml | 0.0333 ml | 0.0333 ml |
| JC Base | 0.8467 gm | 0.8567 gm | 0.8317 gm | 0.8492 gm |

Example 7

A Pilot Study to Examine the Efficacy and Safety of a Tamoxifen Vaginal Suppository in Postmenopausal Hysterectomized Patients with Atrophic Vaginitis The present Example presents the results of a pilot study regarding the efficacy and safety of a Tamoxifen vaginal suppository in postmenopausal hysterectomized patients diagnosed with atrophic vaginitis.

The primary objective of this clinical study was to evaluate the efficacy in treating atrophic vaginitis as determined by an improvement in self-assessment of vaginal dryness, and in normalization of vaginal pH. A secondary objective was to estimate the safety in treating atrophic vaginitis by serum tamoxifen concentration.

Methodology.

Open-label prospective cohort study. Postmenopausal women with atrophic vaginitis were confirmed by vaginal pH. At baseline, vaginal pH and measure of her subjective vaginal dryness based on a VAS vaginal dryness. Four subjects were treated with vaginal suppositories of Tamoxifen for three months. After eight weeks of treatment, subjects had pharmacokinetic studies of the vaginal suppository. After three months of treatment, subjects had a vaginal pH and measure of her subjective vaginal dryness based on a VAS vaginal dryness.

Research Design.

Healthy women with atrophic vaginitis were recruited to this study. To be eligible to enroll in the study, subjects underwent one screening visit. This visit was to determine the subject's vaginal pH and to measure of her subjective vaginal dryness based on a VAS. Once the subject met eligibility criteria, she received study medication.

Subjects received supplies of the study drug every six weeks. The study drug is a vaginal suppository composed of Tamoxifen Citrate 20 mg compounded by a local compounding pharmacist. The formulation of the text compound is provided in Table 10.

TABLE 10

| Tamoxifen Citrate | 0.0200 gm |
|---|---|
| Silica Gel | 0.0150 gm |
| Base JAB: (fatty base) | 1.2485 gm |
| Suppository Volume | 1.2835 gm |
| Citric Acid 0.1% at 0.0013 gm | For pH Adjustment |

Subjects were instructed to insert the suppository vaginally once per day for one week and then twice per week thereafter. After eight weeks of suppository use, subjects had pharmacokinetic studies obtained. These subjects placed the suppository and remained supine for 1 hour. They then had a serum Tamoxifen concentration 5 hours later. Subjects were also called once per month by the pharmacist to address any questions or concerns. At three months, subjects returned for repeat vaginal pH, and an assessment of vaginal dryness as determined by VAS.

Diagnosis and Main Criteria for Inclusion:

1. The study population will include women of all races without a uterus.
2. The presence of vaginal dryness on study visit 1.
3. A vaginal pH greater than 5 on study visit 1.
4. A normal mammogram within one year prior to study visit 1, per subject self report.
5. The patient is able to use the vaginal suppository.
6. The following washout periods before baseline assessments are made are for subjects previously on estrogen alone or estrogen/progestin containing products:
   1 week or longer for prior vaginal hormonal products (rings, creams, gels);
   4 weeks or longer for prior transdermal estrogen alone or estrogen/progestin products;
   8 weeks or longer for prior oral estrogen and/or progestin therapy;
   8 weeks or longer for prior intrauterine progestin therapy;
   3 months or longer for prior progestin implants and estrogen-alone injectable drug therapy;
   6 months or longer for prior estrogen pellet therapy or progestin injectable drug therapy.

Duration of Treatment.

Participants were given the vaginal suppository every day for one week and then two times per week thereafter for 3 months. They were told how to insert the test drug (using the applicator, place the study drug deep into the vagina) and the dosing schedule.

Criteria for Evaluation.

The primary efficacy endpoints were normalization of vaginal pH and improvement in vaginal dryness symptom. Safety assessments consisted of monitoring and recording all adverse events and serious adverse events. The blood concentrations of Tamoxifen were measured after 8 weeks of vaginal administration. The blood tests were measured after 5 hours after vaginal administration.

Statistical Methods.

The primary endpoints are changes in the self-assessment of vaginal dryness and vaginal pH defined as the difference between the baseline and the 3-month measurements. Descriptive statistics provided for the continuous study endpoints will include mean, median, standard deviation, and 95% confidence intervals. Descriptive statistics provided for categorical endpoints will include frequencies, percents, and 95% confidence intervals. Missing values of a variable will be imputed using the last observed value for the participant. Descriptive statistics will be provided with and without imputation of missing values.

The secondary endpoint was the measurement of Tamoxifen concentrations after 8 weeks of administration. Descriptive analysis provided for the continuous study endpoints which will also include mean.

Efficacy Results.

The aim of the pilot study was to estimate the efficacy and safety of the composition in the management of postmenopausal women with atrophic vaginitis. Four subjects have completed the study. Those subjects had a mean age of 55.5 years, range 52-63, and a mean of 7.7 years post-menopause, range 2-15 years. All subjects were white. Vaginal atrophy was present in all cases at baseline.

At baseline, the median vaginal pH was 7.1, with a range of (6.5-7.5). At month 3, the median vaginal pH was 5.0 with a range of (5.0-5.2). The paired difference between baseline and month 3 had a median of −2.0, with a range of −2.5--1.5. The p-value of this paired difference, using the Wilcoxon signed rank test, was 0.07 (Table 11). This is an important finding because vaginal pH using conjugated estrogens vaginal cream given three times per week decreased to 5.2 after 4 months of treatment [Marx et al., Maturitas 2004; 47: 47-54]. Our results are clinically meaningful because they demonstrate that PT-101 was as effective as conjugated estrogens in lowering vaginal pH after only 3 months of treatment and only administered on a twice per week regimen.

The self-assessment of vaginal dryness improved between baseline and month 3. At baseline, the median baseline vaginal dryness rating was 8.0, with a range of (7.5-9.0). At month 3, the median vaginal dryness rating was 3.0, with a range of (2.0-3.0). The paired difference between baseline and month 3 had a median of −5.5, with a range of (−6.0--4.5). The p-value of this paired difference, using the Wilcoxon signed rank test, was <0.07 (Table 11). Our findings are clinically meaningful because vaginal dryness is voiced as the most bothersome problem in sexually active women who find coital activity uncomfortable because of inadequate lubrication. Our finding is in agreement with other estrogen preparations demonstrating that an estrogen agonist is efficacious in the treatment of vaginal dryness resulting from vaginal atrophy [Casper et al., Int Urogynecol J Pelvic Floor Dysfunct 1999; 10: 171-176; Eriksen et al., Eur J Obstet Gynecol Reprod Biol 1992; 44: 137-14470, 71].

TABLE 11

Median pH score and vaginal dryness symptom score, and paired differences between the enrollment and month 3 visits.

| | N | Median* | Range* | P† |
|---|---|---|---|---|
| pH Enrollment | 4 | 7.1 | 6.5-7.5 | |
| pH Month 3 | 4 | 5.0 | 5.0-5.2 | |
| Paired Difference | 4 | −2.0 | −2.5--1.5 | 0.07 |
| Vaginal Dryness Enrollment | 4 | 8.0 | 7.5-9.0 | |
| Vaginal Dryness Month 3 | 4 | 3.0 | 2.0-3.0 | |
| Paired Difference | 4 | −5.5 | −6.0--4.5 | 0.07 |

*A negative value indicates a decrease from enrollment whereas a positive value indicates an increase from enrollment
†P-value from Wilcoxon signed rank test which compared the enrollment value to the 2- and/or 12-week value for each participant.

Safety Results.

All patients who received study medication received the composition completed their visits for treatment and evaluation. There were no patient drop-outs, serious adverse events, or deaths during this study. There were no reported induction or worsening of vasomotor symptoms (climacteric) such as hot flashes with treatment with the test composition. There were no reported side effects or changes to vital signs following treatment with the test composition.

In view of the long-term perspective of vaginal therapy with the test compound in the treatment of urogenital atrophy, it was important to evaluate the initial pharmacokinetic profile during a maintenance therapy regimen. All pharmacokinetic studies for selective estrogen receptor modulator preparations have been measured from an oral route of administration.

Following a single oral dose of 20 mg tamoxifen (PDR. 61 Edition. 2007: Tamoxifen: p3527), an average peak plasma concentration of 40 ng/ml (range 35 to 45 ng/ml) occurred approximately 5 hours after dosing. The average steady state plasma concentration of tamoxifen after administration once daily for 3 months is 122 ng/ml (range 71-183 ng/ml). After initiation of therapy, steady state concentrations for tamoxifen are achieved in about 4 weeks.

The serum concentrations of the composition after 8 weeks of vaginal administration was evaluated. Following a single dose of the composition, we found an average plasma concentration of 5.6 ng/ml with a range of 1.0-10.0 ng/ml, taken approximately 5 hours after dosing [Table 12]. Our finding of a lower mean peak serum concentration (8-fold reduction) and a lower mean steady state serum concentration (25-fold reduction) with the test composition is clinically meaningful because it suggests that there should be less systemic side effects (deep venous thrombosis) associated with the therapy when compared to an oral route of administration.

TABLE 12

Bioavailability of PT-101 after 8 weeks of Administration

| Patient | Serum PT-101 (ng/ml) |
|---|---|
| 001 | 10.0 |
| 002 | 9.6 |
| 003 | 1.0 |
| 004 | 2.0 |
| Mean | 5.6 |

Conclusion.

This open-label prospective cohort clinical study demonstrated that the application of the test compound in women suffering atrophic vaginitis is highly efficacious in improving vaginal pH and vaginal dryness. The application of the test compound seems to produce initial pK profiles that demonstrate that the use of the test compound does not result in meaningful systemic absorption giving us reason to believe that there is little if any risk of venous thrombosis (as associated with oral therapy) associated with the use of this product candidate. In view of the increasing demand for a safe treatment for atrophic vaginitis seen in the menopause, and in keeping with reports of the excessive breast stimulation following estrogen preparations in current use, the test compound is worth special consideration since it seems to be the promising approach to a safe therapy in breast cancer risk patients. Finally, the data demonstrates that the application of the test compound was well tolerated and patient were generally satisfied with the product candidate as demonstrated by the low incidence of adverse events, adverse event discontinuations, ease of use and high compliance with study and medication.

The present invention is not limited in scope by the specific embodiments described herein. Indeed, various modifications of the invention in addition to those described herein will become apparent to those skilled in the art from the forgoing description and the accompanying figures. Such modifications are intended to fall within the scope of the appended claims.

Patents, patent application, publications, product descriptions, and protocols are cited throughout this application, the disclosures of which are incorporated herein by reference in their entireties for all purposes.

What is claimed is:

1. A method of treating atrophic vaginitis or symptoms of atrophic vaginitis in a patient in need thereof, the method comprising:
   topically administering to vaginal tissue patients suffering from atrophic vaginitis a pharmaceutical composition comprising:
      a pharmaceutically effective unit dose of a sole active agent to treat atrophic vaginitis or its symptoms, wherein the sole active agent consists of tamoxifen citrate, and wherein the amount of tamoxifen citrate in the unit dose is from about 1 mg to about 20 mg; and
      an effective amount of a suitable carrier for vaginal administration,
   wherein atrophic vaginitis in the patient comprises at least one symptom selected from the group consisting of a blood level measurement of Folic-Stimulating Hormone (FSH) greater than 40 mIU/ml, a vaginal pH greater than 5 and a Vaginal Maturation Index (VMI) score less than 50.

2. The method of claim 1, wherein the unit dose of tamoxifen citrate is from about 1 mg to about 10 mg.

3. The method of claim 1, wherein the unit dose of tamoxifen citrate is about 5 mg.

4. The method of claim 1, wherein the unit dose of tamoxifen citrate is about 2 mg.

5. The method of claim 1, wherein the unit dose of tamoxifen citrate is about 1 mg.

6. The method of claim 1, wherein the pharmaceutical composition is in a dosage form selected from the group consisting of a vaginal tablet, vaginal suppository, vaginal cream, vaginal gel, and vaginal ring.

7. The method of claim 1, wherein the pharmaceutical composition is administered daily.

8. The method of claim 1, wherein the pharmaceutical composition is administered once a week.

9. The method of claim 1, wherein the pharmaceutical composition is administered twice a week.

10. The method of claim 1, wherein the pharmaceutical composition is administered three times a week.

11. The method of claim 1, wherein the pharmaceutical composition is administered for at least 12 months.

12. The method of claim 1, wherein the pharmaceutical composition is administered for at least 3 months.

13. The method of claim 1, wherein the pharmaceutical composition is administered once a day for at least one week.

14. The method of claim 1, wherein the pharmaceutical composition is administered once a day for at least two weeks.

15. A method of treating atrophic vaginitis or symptoms of atrophic vaginitis in a patient in need thereof, the method comprising:
   topically administering to vaginal tissue patients suffering from atrophic vaginitis a pharmaceutical composition consisting essentially of:
      a pharmaceutically effective unit dose of a sole active agent to treat atrophic vaginitis or its symptoms, wherein the sole active agent consists of tamoxifen citrate, and wherein the amount of tamoxifen citrate in the unit dose is from about 1 mg to about 20 mg; and
      an effective amount of a suitable carrier for vaginal administration,
   wherein atrophic vaginitis in the patient comprises at least one symptom selected from the group consisting of a blood level measurement of Folic-Stimulating Hormone (FSH) greater than 40 mIU/ml, a vaginal pH greater than 5 and a Vaginal Maturation Index (VMI) score less than 50.

* * * * *